US006754298B2

(12) United States Patent
Fessler

(10) Patent No.: US 6,754,298 B2
(45) Date of Patent: Jun. 22, 2004

(54) METHOD FOR STATISTICALLY RECONSTRUCTING IMAGES FROM A PLURALITY OF TRANSMISSION MEASUREMENTS HAVING ENERGY DIVERSITY AND IMAGE RECONSTRUCTOR APPARATUS UTILIZING THE METHOD

(75) Inventor: Jeffrey A. Fessler, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 10/368,534

(22) Filed: Feb. 18, 2003

(65) Prior Publication Data

US 2003/0156684 A1 Aug. 21, 2003

Related U.S. Application Data

(60) Provisional application No. 60/358,233, filed on Feb. 20, 2002.

(51) Int. Cl.[7] .................................................. A61B 6/03
(52) U.S. Cl. ................................ 378/4; 378/15; 378/94
(58) Field of Search ........................... 378/4, 8, 15, 19, 378/94

(56) References Cited

U.S. PATENT DOCUMENTS

| 4,029,963 | A | | 6/1977 | Alvarez et al. | |
|---|---|---|---|---|---|
| 6,507,633 | B1 | | 1/2003 | Elbakri et al. | |
| 2003/0235265 | A1 | * | 12/2003 | Clinthorne et al. | ............ 378/4 |

OTHER PUBLICATIONS

De Man, Bruno, et al., An Iterative Maximum–Likelihood Polychromatic Algorithm For CT, IEEE Tr. Med. Im., 20 (10) : 999–1008, Oct. 2001, pp. 999–1008.
Kinahan, P.E., et al., Attenuation Correction For A Combined 3D PET/CT Scanner, Med. Phys., 25 (10) : 2046–53, Oct. 1998, pp. 2046–2053.

Markham, Charles, et al., Element Specific Imaging In Computerised Tomography Using A Tube Source of X–Rays And Low Energy–Resolution Detector System, Nucl. Instr. Meth., A324 (1) : 383–8, Jan. 1993.
Kotzki, P.O., et al., Prototype of Dual Energy X–Ray Tomodensimeter For Lumbar Spine Bone Mineral Density Measurement: Choice Of The Reconstruction Algorithm And First Experimental Results, Phys. Med. Biol., 1992, vol. 37, No. 12, pp. 2253–2265.
Clinthorne, Neal, A Constrained Dual–Energy Reconstruction Method For Material–Selective Transmission Tomography, Nucl. Instr. Meth. Phys. Res. A., 351 (1) : 347–8, Dec. 1994.
Sukovic, Predrag, et al., Design Of An Experimental System For Dual Energy X–Ray CT, In Proc. IEEE Nuc. Sci. Symp. Med. Im. Conf., vol. 2, pp. 1021–2, 1999.
Sukovic, Predrag, et al., Penalized Weighted Least–Squares Image Reconstruction For Dual Energy X–Ray Transmission Tomography, IEEE Tr. Med. Im., 19 (11) : 1075–81, Nov. 2000.
Gleason, S.S., et al. Reconstruction Of Multi–Energy X–Ray Computed Tomography Images of Laboratory Mice, IEEE Tr. Nuc. Sci., 46 (2) : 1081–6, Aug. 1999.

* cited by examiner

Primary Examiner—David V. Bruce
(74) Attorney, Agent, or Firm—Brooks Kushman P.C.

(57) ABSTRACT

A method for statistically reconstructing images from a plurality of transmission measurements having energy diversity and image reconstructor apparatus utilizing the method are provided. A statistical (maximum-likelihood) method for dual-energy X-ray CT accommodates a wide variety of potential system configurations and measurement noise models. Regularized methods (such as penalized-likelihood or Bayesian estimations) are straightforward extensions. One version of the algorithm monotonically decreases the negative log-likelihood cost function each iteration. An ordered-subsets variation of the algorithm provides a fast and practical version. The method and apparatus provide material characterization and quantitatively accurate CT values in a variety of applications. The method and apparatus provide improved noise/dose properties.

40 Claims, 7 Drawing Sheets

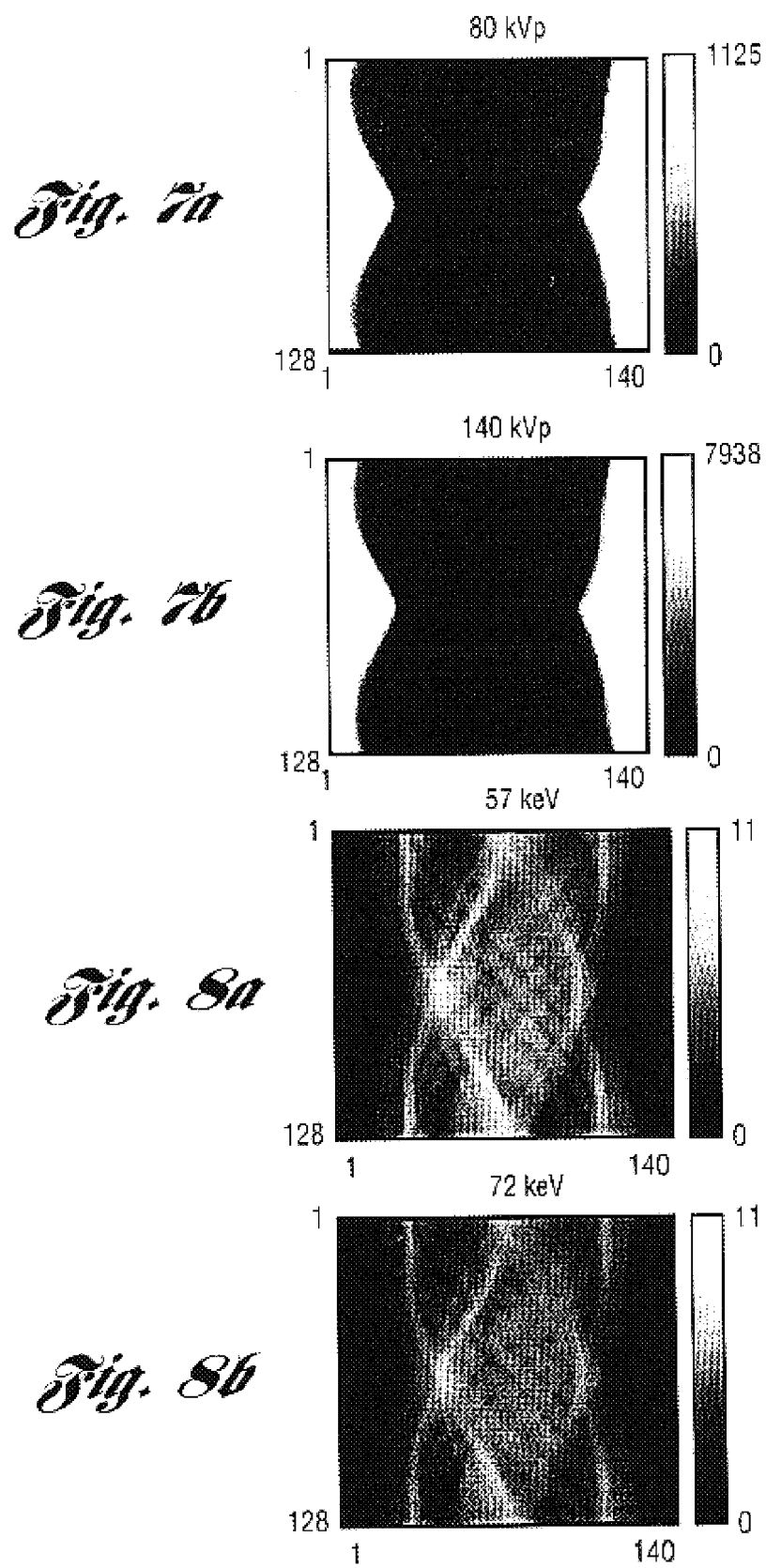

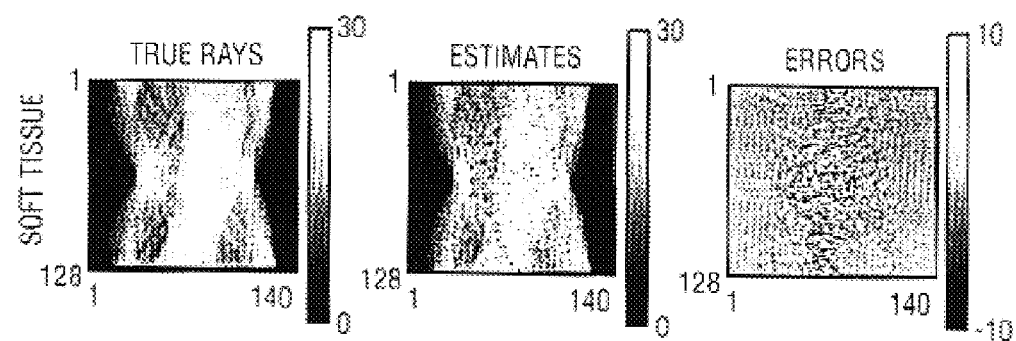
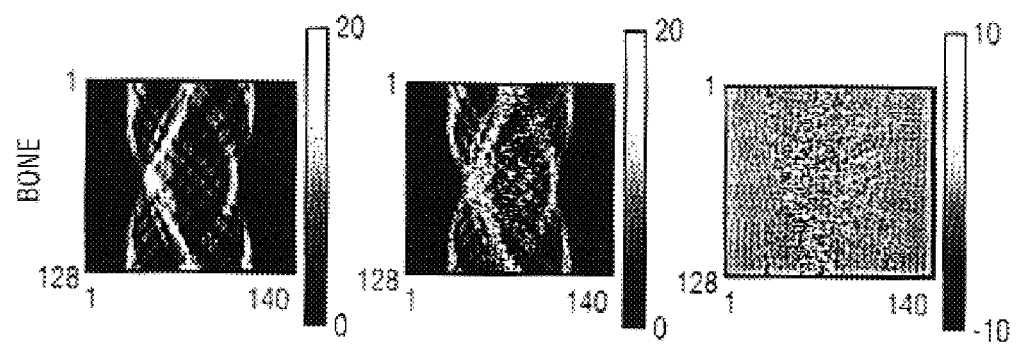
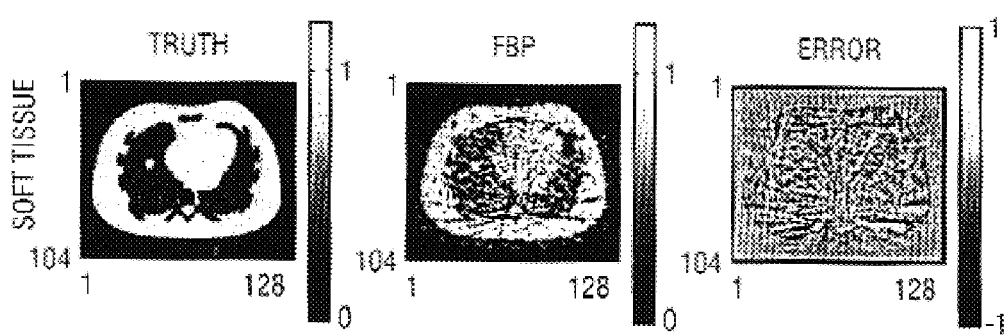
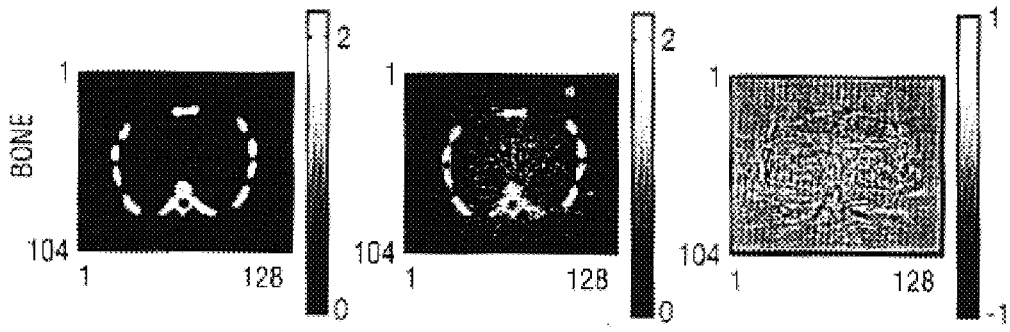

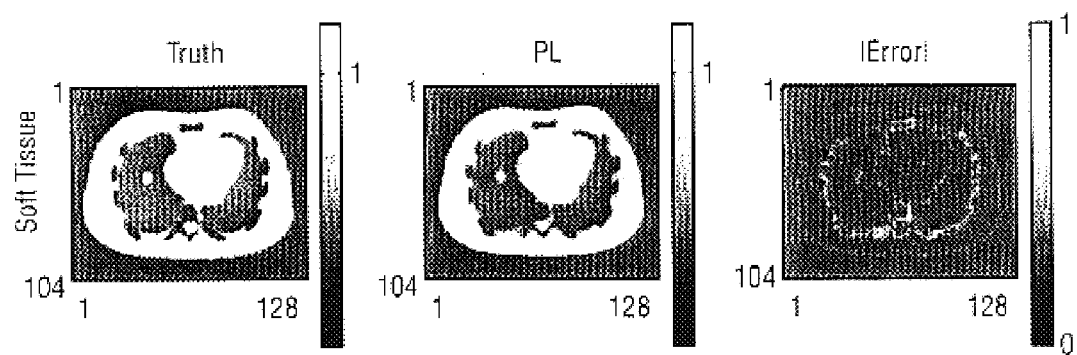
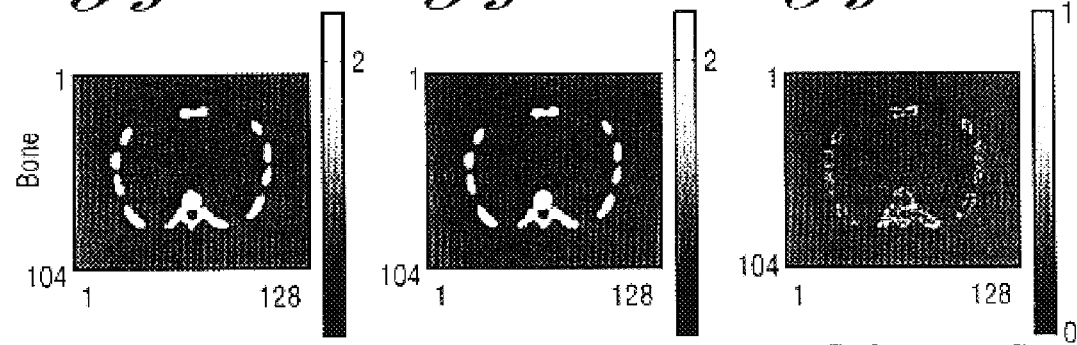
Fig. 11a  Fig. 11b  Fig. 11c
Fig. 11d  Fig. 11e  Fig. 11f
Fig. 12
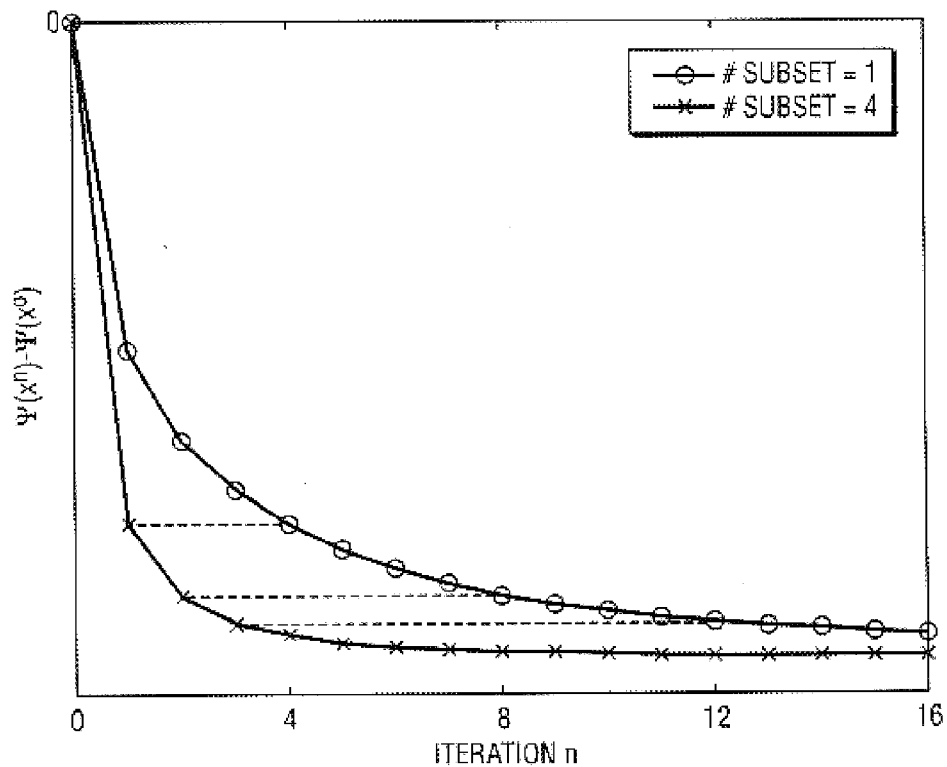

METHOD FOR STATISTICALLY RECONSTRUCTING IMAGES FROM A PLURALITY OF TRANSMISSION MEASUREMENTS HAVING ENERGY DIVERSITY AND IMAGE RECONSTRUCTOR APPARATUS UTILIZING THE METHOD

CROSS-REFERENCE TO RELATED APPLICATION

This application claims the benefit of U.S. provisional application Serial No. 60/358,233, filed Feb. 20, 2002.

STATEMENT REGARDING FEDERALLY SPONSORED RESEARCH OR DEVELOPMENT

This invention was made with government support under NIH Grant Nos. CA 60711 and CA 65637. The Government has certain rights in the invention.

BACKGROUND OF THE INVENTION

1. Field of the Invention

The present invention relates to methods for statistically reconstructing images from a plurality of transmission measurements such as scans having energy diversity and image reconstructor apparatus utilizing the method. The invention can accommodate a wide variety of system configurations and measurement noise models including X-ray CT scanners and systems that use gamma sources with multiple energies, such as some SPECT transmission scans.

2. Background Art

Tomographic images of the spatial distribution of attenuation coefficients in the human body are valuable for medical diagnosis. Most hospitals have CT scanners for producing such images. Attenuation images are also useful in a variety of scientific studies, in industry for non-destructive evaluation, and for security purposes like baggage inspection. X-ray CT scanners are also being integrated into SPECT and PET scanners to provide accurate attenuation correction for emission image reconstruction and for precise anatomical localization of the functional features seen in the emission images.

Material attenuation coefficients depend on the energy of the incident photons. In clinical X-ray CT imaging, the source of the X-ray photons, bremsstrahlung radiation, has an inherently broad energy spectrum. Each photon energy is attenuated differently by the object (body). When such transmission measurements are processed by conventional image reconstruction methods, this energy-dependent effect causes beam-hardening artifacts and compromises quantitative accuracy. To avoid these difficulties, one could employ a radioisotope source with a monoenergetic spectrum, but the practical intensity is usually much lower leading to lower SNR. Recently developed fluorescence-based X-ray sources have somewhat improved intensity but still are lower than clinical CT sources. Higher intensities are obtained from monoenergetic synchrotron sources, which are expensive currently. Many gamma-emitting radioisotopes also emit photons at several photon energies.

U.S. Pat. No. 6,507,633 discloses a statistical method for reconstructing images from a single measured X-ray CT sinogram. That method was the first statistical approach to include a complete polyenergetic source spectrum model in a penalized-likelihood framework with a monotonically converging iterative algorithm. DeMan et al. in "An Iterative Maximum-Likelihood Polychromatic Algorithm for CT," IEEE TR. MED. IM., 20(10):999–1008, October 2001 also proposed a solution to that problem based on a somewhat different object model and an algorithm that may not be monotonically converging. When only a single sinogram (for a given polyenergetic source spectrum) is available, usually one must make some fairly strong assumptions about the object's attenuation properties to perform reconstruction. For example, one may segment the object into soft tissue and bone voxels or mixtures thereof.

The energy dependence of attenuation coefficients is an inconvenience in conventional X-ray CT. Alvarez and Macovski, as disclosed in U.S. Pat No. 4,029,963, showed how to approximate the energy dependence of attenuation coefficients in terms of a Compton scattering component and a photoelectric absorption component (or, roughly equivalently, electron density and atomic number) and how to separate these two components in the sinogram domain prior to tomographic reconstruction. The separate component images could then be combined to synthesize a displayed CT image at any energy of interest. Later enhancements included noise suppression, considerations in basis material choices, energy optimization, beam-hardening assessment and correction, algorithm acceleration, scatter correction, and evaluation of precision.

Numerous potential applications of dual-energy imaging have been explored, including rock characterization for petrochemical industrial applications, soil sample analysis in agriculture, bone mineral density measurements, bone marrow composition, adipose tissue volume determinations, liver iron concentration, explosives detection, detection of contrast agents in spinal canal, non-destructive evaluation, body composition, carotid artery plaques, and radioactive waste drums. Accurate correction of Compton scatter in X-ray CT may also benefit from dual-energy information.

More recently, there has been considerable interest in using X-ray CT images to correct for attenuation in SPECT and PET image reconstruction. In these contexts, one must scale the attenuation values in the X-ray CT images and from the X-ray photon energies to the energies of the gamma photons used in SPECT and PET imaging. Kinahan et al. in "Attenuation Correction for a Combined 3D PET/CT Scanner," MED. PHYS., 25(10):2046–53, October 1998 have noted that accurate scaling from X-ray to PET energies may require dual-energy X-ray CT scans. This is particularly challenging in the "arms down" mode of PET scanning. If the primary purpose of the dual-energy X-ray CT scan is PET attenuation correction (rather than diagnosis), then one would like to use low X-ray doses, resulting in the need for statistical image reconstruction methods to minimize image noise.

The conventional disadvantage of dual-energy methods is the increased scan time if two (or more) separate scans are acquired for each slice. This doubling in scan time can be avoided by methods such as alternating the source energy spectra between each projection angle or between each slice or conceivably in other arrangements. Special split detectors have also been proposed.

Prior to the 1990's, all work on dual-energy X-ray CT used the FBP reconstruction method. In the early 1990's, there were a few iterative methods published for dual-energy CT reconstruction. An iterative method to achieve beam-hardening correction and decomposition into basis materials is known. Markham and Fryar in "Element Specific Imaging in Computerized Tomography Using a Tube Source of X-Rays and a Low Energy-Resolution Detector System," NUCL. INSTR. METH., A324(1):383–8, January 1993 applied the ART algorithm. Kotzki et al. in "Prototype of Dual Energy X-Ray Tomodensimeter for Lumbar Spine Bone Mineral Density Measurements; Choice of the Reconstruction Algorithm and First Experimental Results," PHYS. MED. BIOL., 37(12):2253–65, December 1992 applied a conjugate gradient algorithm. These iterative approaches treat the problem as "finding the solution to a system of equations." These algebraic approaches can improve the accuracy relative to FBP methods, but they do not directly address the radiation dose issue. In contrast, in statistical image reconstruction approaches, the problem is posed as finding the images that best fit the measurements according to the (possibly nonlinear) physical model and a statistical model. Proper statistical modeling can lead to lower noise images, thereby enabling reductions in X-ray dose to the patient.

Statistical approaches have been extensively investigated, particularly in the last ten years, for monoenergetic transmission measurements. Recently, Clinthorne and Sukovic have investigated iterative algorithms for dual-energy and triple-energy CT reconstruction based on a weighted least-squares approach, including object-domain constraints in the following papers:

"A Constrained Dual-Energy Reconstruction Method for Material-Selective Transmission Tomography," NUCl. INSTR. METH. PHYS. RES. A., 351(1):347–8, December 1994;

"Design of an Experimental System for Dual-Energy X-Ray CT," In PROC. IEEE NUC. SCI. SYMP. MED. IM. CONF., Vol. 2, pp. 1021–2, 1999; and "Penalized Weighted Least-Squares Image Reconstruction in Single and Dual-Energy X-Ray Computed Tomography," IEEE TR. MED. IM., 19(11):1075–81, November 2000.

That work assumed monoenergetic measurements. Gleason et al., in the paper "Reconstruction of Multi-Energy X-Ray Computer Tomography Images of Laboratory Mice," IEEE TR. NUC. SCI., 46(2):1081–6, August 1999 hint at the need for ML solutions to the multi-energy problem. Table 1 summarizes the various dual-energy reconstruction methods:

TABLE 1

PRIOR ART DUAL-ENERGY X-RAY CT RECONSTRUCTION METHODS

| Reconstruction Algorithm | Data Preprocessed | Unprocessed |
|---|---|---|
| FBP | Alvarez & Macovski, 1976 (many others since) | — |
| Algebraic | Kotzi et al., 1992 Markham et al., 1993 | — |
| Statistical (Monoenergetic) | | Clinthorne & Sukovic 2000 |

SUMMARY OF THE INVENTION

An object of the present invention is to provide a method for statistically reconstructing images from a plurality of transmission measurements having energy diversity and image reconstructor apparatus utilizing the method wherein, by using multiple measurements with "energy diversity," i.e., a set of two or more energy spectra, one can avoid segmentation, eliminating one potential source of errors.

In carrying out the above object and other objects of the present invention, a method for statistically reconstructing images from a plurality of transmission measurements having energy diversity is provided. The method includes providing a plurality of transmission measurements having energy diversity. The method also includes processing the measurements with an algorithm based on a statistical model which accounts for the energy diversity to obtain at least one final component image which has reduced noise.

The method may further include providing a cost function based on the statistical model. The cost function may be minimized during the step of processing.

The cost function may have a gradient which is calculated during the step of processing. The gradient may be calculated by backprojecting.

The method may further include analyzing the at least one final component image.

The method may further include calibrating spectra of the measurements to obtain calibration data. The step of processing may utilize the calibration data.

The method may further include displaying the at least one final component image.

The gradient may be calculated by approximately using a subset of the measurements, such as an ordered subset of projection views, to accelerate the algorithm.

The cost function may have a regularizing penalty term.

The measurements may be dual-energy X-ray CT scans or may be transmission scans with differing energy spectra, such as X-ray sources with different tube voltages or different filtrations, or gamma-ray sources with multiple energies.

The cost function may include a log-likelihood term.

The cost function may consist solely of a log-likelihood function, which is called maximum likelihood reconstruction, or the cost function may consist of both a log-likelihood function and a regularizing penalty function, which is called penalized-likelihood or maximum a posteriori image reconstruction.

The method may further include preprocessing the measurements prior to the step of processing to obtain preprocessed measurements. The preprocessed measurements may be processed in the step of processing to obtain the at least one component image.

The log likelihood term may be a function that depends on a model for an ensemble mean of the transmission measurements, and the model incorporates characteristics of an energy spectrum.

The log-likelihood term may be a function of the transmission measurements, prior to any pre-processing such as taking a logarithm of the measurements.

The gradient of the cost function may be calculated using a parametric approximation, such as polynomials, tables, or piecewise polynomials.

The regularizing penalty term may be based on quadratic functions of linear combinations of voxel values or nonquadratic (edge-preserving) functions of such combinations.

Parameter constraints such as non-negativity of voxel values may be enforced during or after minimization of the cost function.

The processing step may be based on the preprocessed measurements and may use a cost function based on a statistical model for variability of the preprocessed measurements.

Further in carrying out the above objects and other objects of the present invention, an image reconstructor apparatus for statistically reconstructing images from a plurality of transmission measurements having energy diversity is provided. The apparatus includes means for providing a plurality of transmission measurements having energy diversity. The apparatus further includes means for processing the measurements with an algorithm based on a statistical model which accounts for the energy diversity to obtain at least one final component image which has reduced noise.

The apparatus may further include means for providing a cost function based on the statistical model, and the cost function may be minimized by the means for processing.

The apparatus may further include means for calculating a gradient of the cost function.

The means for calculating may calculate the gradient by backprojecting.

The apparatus may further include means for analyzing the at least one final component image.

The apparatus may further include means for calibrating spectra of the measurements to obtain calibration data, and the means for processing may utilize the calibration data.

The apparatus may further include a display for displaying the at least one final component image.

The means for calculating may calculate the gradient approximately using a subset of the measurements, such as an ordered subset of projection views, to accelerate the algorithm.

The cost function may have a regularizing penalty term.

The measurements may be transmission scans with differing energy spectra, such as X-ray sources with different tube voltages or different filtrations, or gamma-ray sources with multiple energies.

The cost function may include a log-likelihood term, or the cost function may consist of both a log-likelihood function and a regularizing penalty function, which is called penalized-likelihood or maximum a posteriori image reconstruction.

The cost function may include a maximum likelihood or penalized likelihood algorithm.

The apparatus may further include means for preprocessing the measurements to obtain preprocessed measurements. The preprocessed measurements may be processed by the means for processing to obtain the at least one component image.

The log likelihood term may be a function that depends on a model for an ensemble mean of the transmission measurements, and the model incorporates characteristics of an energy spectrum.

The log-likelihood term may be a function of the transmission measurements, prior to any pre-processing such as taking a logarithm of the measurements.

The gradient of the cost function may be calculated using a parametric approximation, such as polynomials, tables, or piecewise polynomials.

The regularizing penalty term may be based on quadratic functions of linear combinations of voxel values or nonquadratic (edge-preserving) functions of such combinations.

Parameter constraints such as non-negativity of voxel values may be enforced during or after minimization of the cost function.

The means for processing may process the preprocessed measurements and may use a cost function based on a statistical model for variability of the preprocessed measurements.

The above objects and other objects, features, and advantages of the present invention are readily apparent from the following detailed description of the best mode for carrying out the invention when taken in connection with the accompanying drawings.

BRIEF DESCRIPTION OF THE DRAWINGS

FIGS. 7a and 7b show simulated dual-energy CT sinogram measurements $Y_{mi}$;

FIGS. 8a and 8b show estimates $\hat{f}_{im}$ computed from noisy simulated dual-energy measurements (i.e., smoothed and log-processed sinogram measurements);

FIGS. 9a–9f show estimates $\hat{s}_i$ computed from noisy simulated dual-energy measurements;

FIGS. 10a–10f show FBP dual-energy reconstructions of soft tissue and bone components;

FIGS. 11a–11f show penalized likelihood dual-energy reconstructions of soft tissue and bone components; the density units are 1/cm; and FIG. 12 shows graphs of cost function decrease versus iteration n for 1-subset and 4-subset algorithms with precomputed denominator.

DETAILED DESCRIPTION OF THE PREFERRED EMBODIMENTS

Figure 1A:
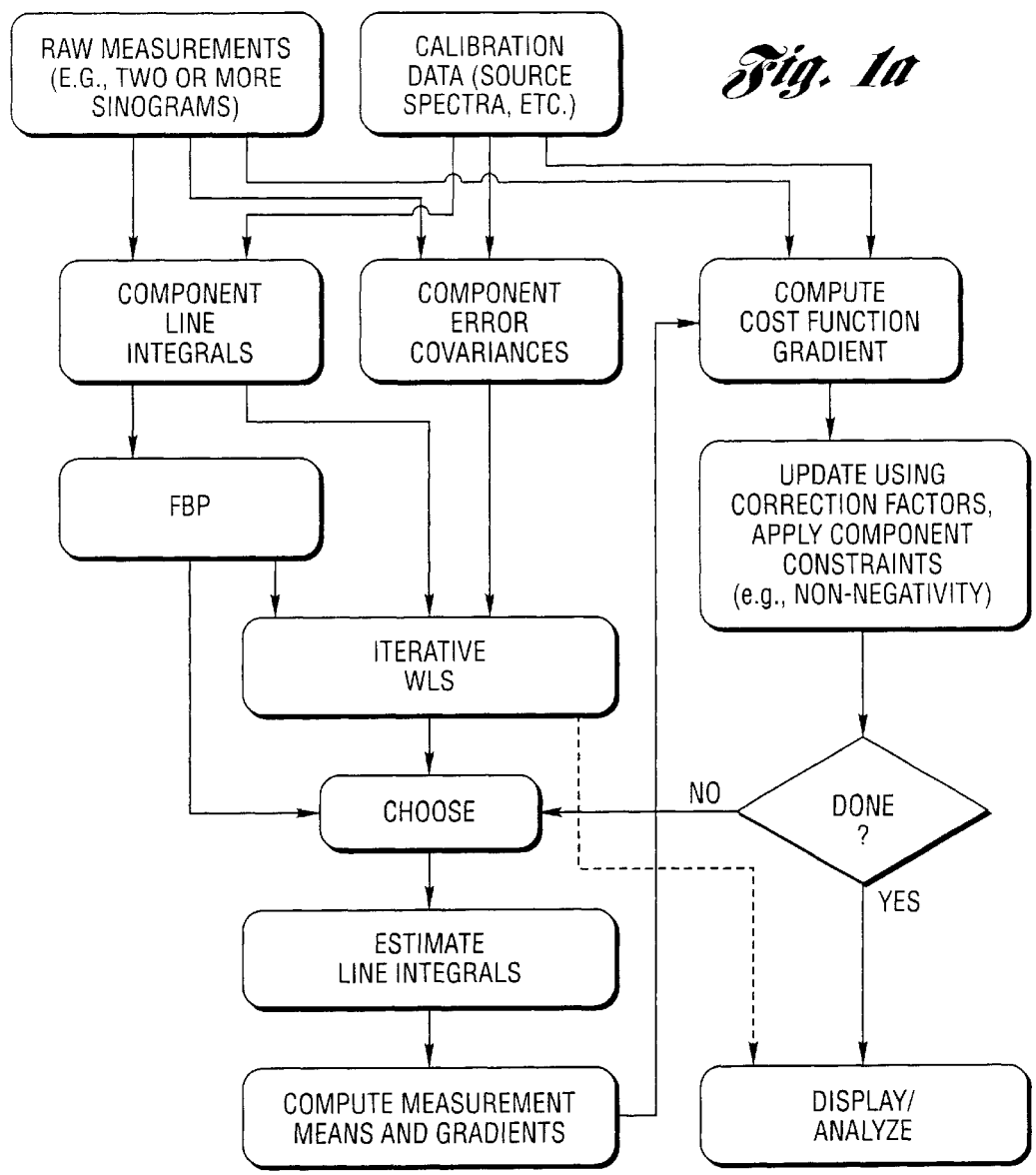
FIG. 1a is a block diagram flow chart illustrating a statistically polyenergetic reconstruction method of the present invention.

In general, the method described herein is a novel extension of statistical image reconstruction approaches from the monoenergetic case to the case of measurements with energy diversity. A statistical (maximum likelihood or penalized likelihood) method for reconstructing an "attenuation map" $\mu(\vec{x}, \epsilon)$ from polyenergetic X-ray (or gamma-ray) tomographic measurements is described herein.

Like most dual-energy reconstruction methods, the method of the invention typically requires some knowledge about the X-ray beam spectrum. This spectrum can be measured directly or estimated from calibration phantoms. In the final analysis, rather than requiring the entire spectrum, the algorithm typically requires only the nonlinear function $f_{im}$ given in Equation (11) below and its derivative. It may be feasible to measure $f_{im}$ empirically for a given scanner. The method does not exhibit inordinate sensitivity to imperfections in the source spectrum model.

Physical Models

Let $\mu(\vec{x}, \epsilon)$ denote the object's linear attenuation coefficient as a function of spatial position $\vec{x}$ and photon energy $\epsilon$. The ideal tomographic imaging system would provide a complete description of $\mu$ for $\vec{x}$ in the entire field of view and for a wide range of energies $e$. In practice, the goal is to reconstruct an estimate of a from a finite collection of "line-integral" measurements. (For simplicity, it is assumed that the object is static, and any temporal variations are ignored, although it is possible to generalize the method to the dynamic case).

A. General Measurement Physical Model

The following general physical model for the measurements is assumed. One collects transmission tomographic measurements with $N_s \geq 21$ different incident spectra, e.g., by changing the X-ray source voltage and/or the source filtration.

Alternately, one could use multiple energy windows in an energy-sensitive detector, such as in SPECT transmission scans with a multi-energy radioisotope. In these cases, there is really only one "incident spectrum," but it is described as a collection of $N_s$ different incident spectra since that is the usual framework in dual-energy X-ray CT.

For each incident spectra, one records tomographic "line integrals" at $N_d$ radius-angle pairs, i.e., a sinogram is formed (not necessarily completely sampled). Let $Y_{mi}$ denote the measurement for the ith ray for the mth incident spectrum, $m=1, \ldots, N_s$, $i=1, \ldots, N_d$. For notational simplicity, the case is presented where the same number of rays are recorded for each incident spectrum. The method generalizes easily to the case where the number or configuration of rays is different for different incident spectra, which may be useful in practice. One refers to $\{Y_{mi}\}_{i=1}^{N_d}$ as the measurements for the "mth incident spectrum."

One assumes that the measurements are random variables with the following ensemble means:

$$E_\mu[Y_{mi}] = \bar{y}_{mi} \triangleq \int I_{mi}(\varepsilon)\exp\left(-\int_{L_{mi}} \mu(\vec{x}, \varepsilon)dl\right)d\varepsilon + r_{mi}, \quad (1)$$

where $\int_{L_{mi}} \cdot dl$ dedenotes the "line integral" function for the ith position and the mth energy, and $I_{mi}(\epsilon)$ denotes the product of the source energy spectrum and the detector gain (for the mth incident spectrum), and $r_{mi}$ denotes "known" additive background contributions such as room background, dark current, and/or scatter. This is an idealization since it ignores the nonlinearity caused by the exponential edge-gradient effect. One could extend the algorithm derivation to account for this effect, but for simplicity the polyenergetic aspects are focused on here. Typically $L_{hd\ mi}$ will be independent of m, except in some systems where alternate projection views have different energy spectra. One treats each $I_{mi}(\epsilon)$ and $r_{mi}$ as known and non-negative. Determining $I_{mi}(\epsilon)$ in practice may require careful calibration procedures. One usually determines $r_{mi}$ by some pre-processing steps prior to iterative reconstruction. For example, the $r_{mi}$s may be equated to known constants related to the "shifted Poisson" approach based on detector noise models.

Methods are described herein for reconstructing p from tomographic measurements with energy diversity under log-likelihood models based on the general physical model (1). All previously published approaches have been based on simplifications of (1) or of the associated log-likelihoods with one exception. We first describe those "conventional" simplifications, and then proceed to describe the new approach.

B. Basis Material Decomposition (Object Model)

One has only a finite set of measurements whereas $\mu$ is a continuous function of energy and spatial location. Parametric statistical estimation requires some form of discretization of $\mu$. For the polyenergetic case, one must parameterize both the spatial and energy dependencies. To our knowledge, all prior work has considered parameterizations that use basis functions that are separable in the spatial and energy (or material density) dimensions. Separable approaches seem simple and natural. For example, Alvarez and Macovski assume that $$\mu(\vec{x}, \varepsilon) = \sum_{l=1}^{L} f_l(\varepsilon)\alpha_l(\vec{x}), \quad (2)$$

where each $f_l(\epsilon)$ depends only on energy but not on spatial position, $\beta_1(\vec{x})$ is the corresponding coefficient that varies spatially, and L is usually 2. Alternatively, Clinthorne et al. assume that $$\mu(\vec{x}, \varepsilon) = \sum_{l=1}^{L} \beta_l(\varepsilon)\rho_l(\vec{x}), \quad (3)$$

where $\beta_l(\epsilon)$ denotes the energy-dependent mass-attenuation coefficient of the lth material type (e.g., soft tissue, bone mineral, contrast agent, etc.), and $\rho_l(\vec{x})$ is the density of that material at spatial location $\vec{x}$. This latter parameterization facilitates enforcing physical constraints such as non-negativity. Both of the above parameterizations use bases that are separable in space/energy. This separability property is needed for the type of algorithm derived in previous work. The more general algorithm derived in this paper does not require separability. A more general parameterization is described in (23) below after reviewing conventional approaches.

The conventional approach to dual-energy X-ray CT is to substitute (2) or (3) into (1). As described in detail hereinbelow, this yields a system of equations in the line integrals through the spatial basis functions. One can solve these equations numerically in sinogram space, and then perform FBP reconstruction to form images of the material components.

C. Conventional Monoenergetic Approximation

Another way to simplify (1) is to assume that each incident spectrum is monoenergetic. That model is realistic for some radioisotope sources, but is a considerable idealization of X-ray sources. Mathematically, the monoenergetic assumption is expressed $$I_{mi}(\epsilon)=I_{mi}\delta(\epsilon-\epsilon_m), \quad (4)$$

where $\epsilon_m$ denotes the energy of the mth setting, $m=1, \ldots, N_s$. Under this assumption, the model (1) simplifies to $$\bar{y}_{mi}=I_{mi}\exp(-\int L_{mi}\mu(\vec{x}, \epsilon_m)dl)+r_{mi}. \quad (5)$$

In this case, one can estimate the line integrals $l_{mi} \triangleq \int_{L_{mi}} \beta(\vec{x}, \mu_m)dl$ by a simple logarithm:

$$\hat{l}_{mi} \triangleq \log\left(\frac{I_{mi}}{Y_{mi} - r_{mi}}\right) \approx \int_{L_{mi}} \mu(\vec{x}, \varepsilon_m)dl. \quad (6)$$

Again, one could apply the FBP method to reconstruct $\mu(\vec{x}, \epsilon_m)$ from $\{\hat{l}_{mi}\}_{i=1}^{N_d}$.

Clinthorne and Sukovic combined (6) with (3) to formulate a penalized weighted least-squares image reconstruction method for dual-energy and triple-energy tomographic reconstruction. Their simulations matched the monoenergetic model (4), so the question of whether a monoenergetic approximation is adequate for iterative dual-energy tomographic image reconstruction is an open one. The algorithm proposed herein will facilitate comparisons between the fuill polyenergetic treatment and the simpler monoenergetic approximation.

The case of a single monoenergetic measurement, i.e., $N_s=1$ in (4), is the most extensively studied tomographic reconstruction problem, and numerous non-statistical and statistical methods have been proposed for this case.

To estimate ii by iterative statistical methods, one must eventually parameterize it. In the single monoenergetic case, one usually assumes $$\mu(\vec{x}, \varepsilon_1) = \sum_{j=1}^{N_p} b_j(\vec{x})\mu_j \qquad (7)$$

for some spatial basis fuinctions $b_j(\bullet)$, such as indicator functions overreach pixel's support. Substituting into (5) yields $$\overline{y}_{1i} = I_{1i} \exp\left(-\sum_{j=1}^{N_p} a_{ij}\mu_j\right) + r_{1i}, \qquad (8)$$

where $$a_{ij} \triangleq \int_L b_j(\vec{x})d. \qquad (9)$$

The model (8) is used in "conventional" statistical methods for transmission image reconstruction.

D. Beam-Hardening Correction

U.S. Pat No. 6,507,633 discloses a method which combines (3) with the polyenergetic measurement model (1) in the single scan case ($N_s=1$) to develop a statistical method for X-ray CT image reconstruction with compensation for beam-hardening, assuming that the image can be segmented into soft-tissue and bone voxels. This same assumption is used in conventional non-statistical methods for beam-hardening correction. DeMan et al. proposed another statistical method for beam-hardening correction, assuming that all materials in the patient have spectral properties that are linear combinations of two basis materials. An advantage of energy diversity approaches ($N_s > 1$) is that they eliminate the need for segmentation and other approximations that may hinder material characterization.

Preprocessing-Based Methods

Before describing the maximum-likelihood approach of the present invention in detail, two existing "preprocessing" approaches to dual-energy CT reconstruction are described. The first approach is the classical non-statistical method, and the second approach is the recently published weighted least-squares approach, including some extensions of that approach.

A. Conventional Dual-Energ Approach

Substituting (3) into (1) yields the following simplified model for the measurement means:

$$\overline{y}_{mi} = I_{mi}e^{-f_{im}(s_i(\rho))} + r_{mi} \qquad (10)$$

$$f_{im}(s_i) \triangleq -\log\left(\frac{\int I_{mi}(\varepsilon)\exp(-\Sigma_l \beta_l(\varepsilon)s_{il})d\varepsilon}{I_{mi}}\right) \qquad (11)$$

$$s_{il} \triangleq (s_{il}, \ldots, s_{iL}) \qquad (12)$$

$$s_{il}(\rho) \triangleq \int_{L_{mi}} \rho_l(\vec{x}) dl,$$

$$s_i \triangleq (s_{il}, \ldots, s_{iL})$$

$$s_{il}(\rho) \triangleq \int_{L_{mi}} \rho_l(\vec{x}) dl \qquad (12)$$

for $m=1, \ldots, N_s$ and $l=1, \ldots, L$, where the following total intensity is defined as:

$$I_{mi} \triangleq \int I_{mi}(\varepsilon)d\varepsilon. \qquad (13)$$

Given noisy measurements $Y_{mi}$, the natural approach to estimating the $f_{im}$'s is to invert (10):

$$\hat{f}_{im} \triangleq -\log\left(\text{smooth}\left(\frac{Y_{mi} - r_{mi}}{I_{mi}}\right)\right) \approx f_{im}(s_i), \qquad (14)$$

where often some radial smoothing is included to reduce noise. By a Taylor expansion, in the absence of smoothing the variance of these $\hat{f}_{im}$'s is approximately:

$$Var\{\hat{f}_{im}\} \approx \frac{Var\{Y_{mi}\}}{(\overline{y}_{mi} - r_{mi})^2}. \qquad (15)$$

Ignoring measurement noise, in the usual case where $L_{mi}=L_i$ is independent of m, one can view (14) as a system of $N_s$ nonlinear equations in L unknowns for the ith ray, where the lth unknown is $s_{il}$ defined in (12), namely the ith line integral through the lth basis material. If $N_s \geq L$, then for each i, one can solve these nonlinear equations by iterative methods or by polynominal approximation. Mathematically, a natural strategy would be least squares:

$$\hat{s}_i = \arg\min_{s \in R^L} \sum_{m=1}^{N_s} w_{mi} \frac{1}{2}(\hat{f}_{im} - f_{im}(s))^2, \qquad (16)$$

for $i=1, \ldots, N_d$, where $w_{mi}$ is a weighting corresponding to the reciprocal of an estimate of the variance of $\hat{f}_{im}$. Based on (15), a reasonable choice is simply $w_{mi}=Y_{mi}$ if the measurements are approximately Poisson and if the $r_{mi}$'s are small. Usually we have $N_s=L$, and in this case the above least-squares estimator degenerates into simply solving the system of equations (14), yielding estimates $\hat{s}_i$ of the $s_i$'s of the following form:

$$\hat{s}_i \triangleq f_i^{-1}(\hat{f}_i), \qquad (17)$$

where $$f_i \triangleq (f_{il}, \ldots, f_{iN_s}).$$

This is the classical dual-energy "preprocessing" approach. After having estimated the $\hat{s}_i$'S in sinogram space, one must use these $\hat{s}_i$'S to reconstruct images of the basis components (e.g., soft tissue and bone). The classical approach is to apply the FBP method separately to each sinogram $$\{\hat{s}_{il}\}_{i=1}^{N_d}$$

to form estimated component images $\hat{\rho}_l(\vec{x})$. The FBP method usually yields unacceptable noisy estimates of the component images, hampering its acceptance. (Convex combinations of the component images have at best the same SNR as conventional X-ray CT images.)

To understand the source of this noise, it is instructive to analyze the noise properties of (17) or more generally (16). Using error propagation analysis, one can show that the covariance of $\hat{s}_1$ is approximately $$Cov\{\hat{s}_i\} \approx [(\nabla_R f_i) W_i (\nabla_C f_i)]^{-1} (\nabla_R f_i) W_i Cov\{\hat{f}_i\} W_i (\nabla_C f_i) [(\nabla_R f_i) W_i (\nabla_C f_i)]^{-1}, \quad (18)$$

where $W_i = \text{diag}\{w_{mi}\}$ and $\nabla_R$ and $\nabla_C$ denote row and column gradients, respectively. In the usual case where $W_i = Cov\{\hat{f}_i\}^{-1}$ as described above, then this covariance simplifies to $$Cov\{\hat{s}_i\} \approx [(\nabla_R f_i) Cov\{\hat{f}_i\}^{-1} (\nabla_C f_i)]^{-1}, \quad (19)$$

where one evaluates the gradients at the mean of $\hat{s}_i$.

If the $N_s \times L$ matrix $\nabla_R f_i$ had orthogonal columns, then the inversion step (17) would not amplify noise. But in practice $\nabla_R f_i$ can be quite poorly conditioned, and examining its conditioning can provide insight into the challenges in dual-energy CT reconstruction. Note that $$[\nabla_C f_i(s)]_{ml} = \frac{\partial}{\partial s_{il}} f_{im}(s)) = \frac{1}{\overline{y}_{mi} - r_{mi}} \int I_{mi}(\varepsilon) \beta_l(\varepsilon) e^{-\beta'(\varepsilon)s} d\varepsilon.$$

In particular, $$[\nabla_C f_i(s)]_{ml}|_{s=0} = \overline{\beta}_{iml},$$

where the "effective" mass attenuation coefficient is defined as follows:

$$\overline{\beta}_{iml} \triangleq \frac{\int \beta_l(\varepsilon) I_{mi}(\varepsilon) d\varepsilon}{I_{mi}}. \quad (20)$$

One can explore the instability of dual-energy reconstruction by examining $N_s \times L$ matrix $B_i$ with entries $\overline{\beta}_{iml}$ for various material basis functions and source spectra.

Figure 2A:
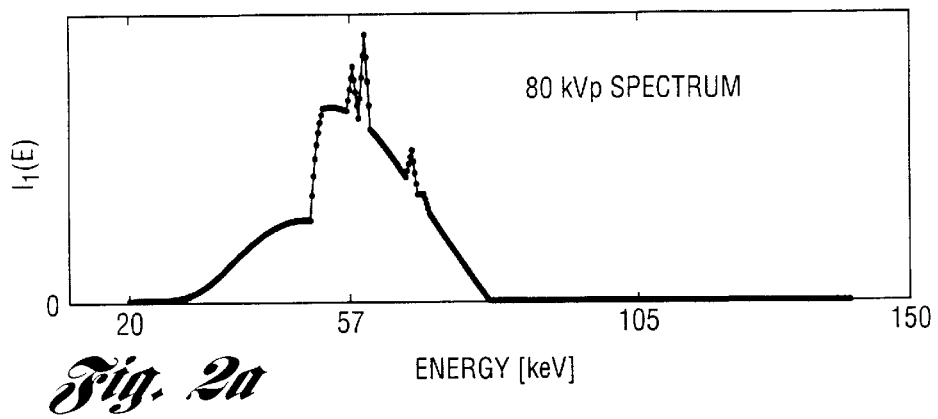
FIGS. 2a and 2b are graphs which show X-Ray source spectra $I_m(\epsilon)$ used in a computer simulation; the dashed vertical lines are located at the effective energy $\bar{\epsilon}_m$ of each spectrum.
Figure 2B:
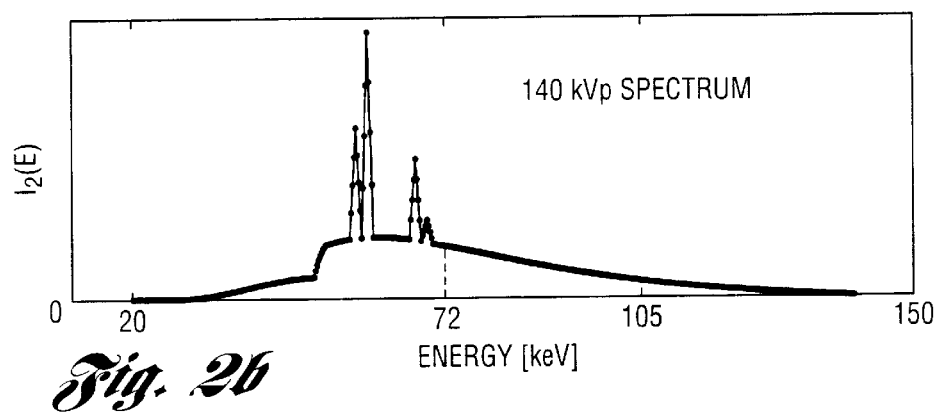
Figure 3:
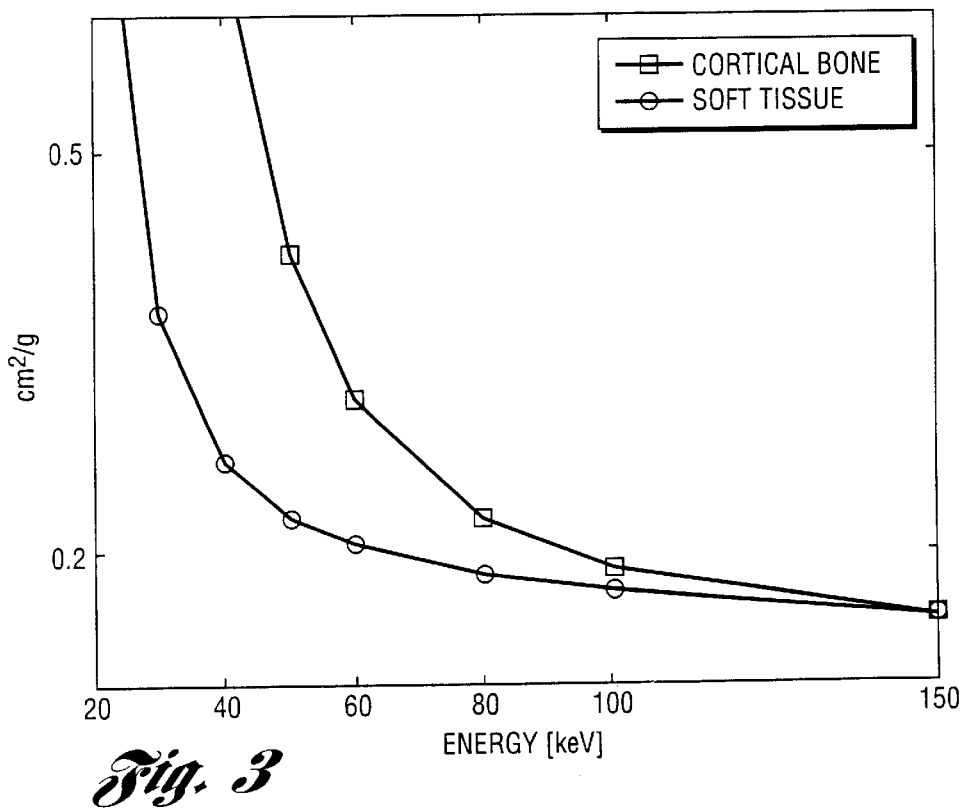
FIG. 3 is a graph which shows mass attenuation coefficients $\beta_l(\epsilon)$ of cortical bone and soft tissue used in computer simulation.

As an example, for the data shown in FIGS. 2a and 2b and FIG. 3, we compute:

$$B_i = \{\overline{\beta}_{iml}\} = \begin{bmatrix} 0.264 & 0.655 \\ 0.199 & 0.309 \end{bmatrix},$$

which has condition number 13.0. Furthermore, the "noise amplification" matrix $[B_i'B_i]^{-1}$ in (19) has diagonal entries that are roughly $10^2$.

B. WLS Approaches

Instead of using FBP to reconstruct $\rho_l(\vec{x})$ from the $\hat{s}_i$'s, an alternative is to use a statistically-motivated reconstruction method such as a penalized weighted least-squares (PWLS) cost function. This approach is similar to that proposed by Clinthorne and Sukovic. The source was assumed to be monoenergetic, so the logarithms of the measurements were used directly. Here, one can account for the polyenergetic spectrum by first estimating the $\hat{s}_i$'s using (16) or (17) in sinogram space. If the source is monoenergetic, then the two variations are equivalent. For polyenergetic sources, (16) or (17) will be more accurate than simple logarithms.

Consider the separable parameterization $$\mu(\vec{x}, \varepsilon) = \sum_{l=1}^{L} \sum_{j=1}^{N_p} \beta_l(\varepsilon) b_j(\vec{x}) x_{lj} \quad (21)$$

where $\beta_l(\varepsilon)$ is the mass attenuation coefficient of the lth material type and $\{b_j(\vec{x})\}$ are spatial basis functions. As before, suppose that $L_{mi}$ is independent of m, i.e., the same rays are collected for each incident energy setting. Then the integral in (12) simplifies as follows:

$$\int_{L_{mi}} \rho_l(\vec{x}) dl = s_{il}(x_l) \triangleq \sum_{j=1}^{N_p} a_{ij} x_{lj}$$

where $a_{ij}$ was defined in (9).

Having estimated the $\hat{s}_i$'s using (16) or (17) in sinogram space, one must then solve for x. A natural statistical approach is to use a PWLS criterion as follows:

$$x = \arg \min_{x \in R^{N_p \times L}} \Psi(x) \quad (22)$$

$$\Psi(x) \triangleq \sum_{i=1}^{N_d} \frac{1}{2} (\hat{s}_i - s_i(x))' W_i(\hat{s}_i s_i(x)) + R(x)$$

where $W_i \in R^L$ is an estimate of the covariance of $$\hat{s}_i, s_i(x) \triangleq (s_{i1}(x_1), \ldots, s_{iL}(x_L)),$$

and

R(x) is a regularization function. There are numerous iterative algorithms suitable for this quadratic minimization problem, such as coordinate descent, or conjugate gradients, or ordered-subsets approaches.

There are three natural choices for the covariance estimates $W_i$. The simplest choice would be unweighted, where each $W_i$ is simply the $L \times L$ identity matrix. Although the most convenient to use, this unweighted choice may provide relatively limited improvement over FBP which is also an unweighted method. The second choice would be to let $W_i$ be diagonal with diagonal entries corresponding to estimates of the variances of the elements of $\hat{s}_i$. This variance weighted approach would reduce noise by giving less weight to the noisier rays. The final approach would be to let $W_i$ be a complete estimate of the $L \times L$ covariance matrix of $\hat{s}_i$, as described in (18). If the source spectra were monoenergetic, then one can show that this latter approach is essentially equivalent to the method of Sukovic and Clinthorne. Thus, the method (22) is essentially a generalization to the polyenergetic case.

The disadvantage of the above PWLS methods relative to the ML approach described hereinbelow is that the nonlinear preprocessing that leads to the $\hat{s}_i$'s obscures their statistical distribution and seems to limit one to least-squares formulations. In contrast, the ML approach can use a very accurate statistical model. However, the ML approach is complicated by the nonlinearity of the physical model (1) and the generality of the statistical models considered.

Statistical Model and Likelihood

This section describes assumptions about the measurement statistics and formulates the log-likelihood.

A. Proposed Polyenergetic Object Model

As noted above, most prior work has considered bases that are separable in the spatial and energy (or material density) dimensions, as in (2) and (3). In the interest of generality here, the algorithm is derived under the following very flexible parameterization:

$$\mu(\vec{x}, \varepsilon) = \sum_{k=1}^{K_b} \chi_k(\vec{x}, \varepsilon) x_k, \quad (23)$$

where $K_b$ is the number of basis functions and $x_k$ is the unknown coefficient of the kth basis function. By taking $K_b$ sufficiently large and using suitably localized $\chi_k$'s, any function $\mu$ can be approximated to arbitrary accuracy by (23). Both of the preceding parameterizations (2) and (3) are special cases of (23). For the usual two-material separable parameterization, we have $K_b = 2N_p$ is the number of voxels. A non-separable basis may be useful for example if a certain material component (such as a metal implant) is known a priori to be present only in certain image locations. This may be useful even for the bone-mineral component a priori segmentation can adequately identify the bone regions.

Using the general parameterization (23), the inner integral in (1) becomes:

$$\int_{L_{mi}} \mu(\vec{x}, \varepsilon) dl = \int_{L_{mi}} \left[ \sum_{k=1}^{K_b} \chi_k(\vec{x}, \varepsilon) x_k \right] dl$$

$$= \sum_{k=1}^{K_b} a_{mik}(\varepsilon) x_k \triangleq [A_m(\varepsilon) x]_i$$

where the coefficient vector $$x \triangleq (x_1 \ldots, x_{K_b}),$$

and where $A_m(\varepsilon)$ is a $N_d \times K_b$ matrix with elements $$[A_m(\varepsilon)]_{ik} = a_{mik}(\varepsilon) \triangleq \int_{L_{mi}} \chi_k(\vec{x}, \varepsilon) dl,$$

for $i=1, \ldots, N_d$, $k=1, \ldots, K_b$. Substituting into (1) yields the following discrete-object discrete-data mean model:

$$\bar{y}_{mi}(x) = \int I_{mi}(\varepsilon) e^{-[A_m(\varepsilon) x]_i} d\varepsilon + r_{mi}. \quad (24)$$

In the absence of noise, our goal would be to estimate x from the measurements $\{Y_{mi}\}$ using the model (24).

B. Statistical Methods

If one used photon-counting detectors with modest deadtimes, then it would be reasonable to assume that the measurements are statistically independent Poisson random variables with means (1), i.e., $$Y_{mi} \sim \text{Poisson } \{\bar{y}_{mi}[x]\}.$$

In this case, for a given measurement realization $Y_{mi} = y_{mi}$, the corresponding negative log-likelihood of x has the form $$-L(x) \equiv \sum_{m=1}^{N_s} \sum_{i=1}^{N_d} \bar{y}_{mi}(x) - y_{mi} \log \bar{y}_{mi}(x),$$

where $\equiv$ means "equal to within irrelevant constants independent of x." This is the model used in most statistical image reconstruction methods for transmission tomography to date and it is natural for photon-counting detectors such as those used in PET and SPECT transmission scans.

Although photon-counting X-ray detectors do exist, commercial X-ray CT systems use current integrating detectors that yield energy-dependent signals and additional electronic noise variance beyond that due to Poisson counting variability. To first order, additive electronic noise can be approximated within the Poisson model using the $r_{mi}$ terms in (1) by a simple modification of the "shifted Poisson" approach. It is likely that the "exact" likelihood for such detectors is analytically intractable, so approximations will undoubtably be used in practice. For example, Clinthorne describes a sophisticated point-process model for X-ray detection and uses its first and second moments. Rather than postulating and attempting to validate any particular approximate statistical model in this application, the algorithms are derived under very general assumptions that will accommodate a wide variety of log-likelihood models and approximations that might be proposed in the future.

The following four assumptions are made about the measurement statistics.

1. The measurements $\{Y_{imi}\}$ are statistically independent. Due to effects like scintillator afterglow and electronics lag, statistical independence may not hold exactly in practice, but it is likely to be an accurate approximation for most X-ray CT systems. Accounting for whatever statistical dependencies may be present in real systems would likely be quite challenging.

2. The marginal negative log-likelihood of $Y_{mi}$ has the form $\psi_{mi}(\bar{y}_{mi}(x))$ for some scalar function $\psi_{mi}$. For example, if the measurements have Poisson distributions, then $$\psi_{mi}(y) = y - y_{mi} \log y. \quad (25)$$

This is perhaps the simplest case, but we allow for much more general $\psi_{mi}$'s in the derivation.

3. The final two assumptions are more technical and concern the existence of convenient surrogate functions for the $\psi_{mi}$'s of interest. It is believed that all physically plausible $\psi_{mi}$'s will satisfy these quite general assumptions. They are certainly satisfied for Poisson and Gaussian statistical models.

For each $\psi_{mi}$, it is assumed that there exists a corresponding scalar surrogate function $h_{mi}(\bullet, \bullet)$ that is convex on $(0, \infty)$ in its first argument. By surrogate function, it is meant a function that satisfies $$h_{mi}(y, y) = \psi_{mi}(y), \quad \forall y > 0 \quad (26)$$

$$h_{mi}(y, z) \geq \psi_{mimi}(y), \quad \forall y > 0. \quad (27)$$

These conditions are the key to deriving an iterative algorithm that monotonically decreases the cost function defined below. For each z>0, it is also assumed that $h_{mi}(\bullet, z)$ is differentiable in its first argument in an open interval around z. This assumption, combined with (26) and (27), ensures the following tangent condition:

$$\dot{h}_{mi}(z, z) = \dot{\psi}_{mi}(z), \quad \forall z > 0, \quad (28)$$

where $$\dot{h}_{\mathrm{mi}}(y, z) \triangleq \frac{\partial}{\partial y} h(y, z).$$

4. Convexity alone may be sufficient for some types of iterative minimization algorithms. However, to enable use of very simple descent methods, we will find parabolic surrogates. The following assumption ensures that the necessary parabola exists, which it certainly does in the Poisson case among others.

For any $x \geq 0$, the function:

$$g_{\mathrm{mi}}(l, x, \varepsilon) \triangleq h_{\mathrm{mi}}(b_{\mathrm{mi}}(x, \varepsilon)e^{-l} + r_{\mathrm{mi}}(x, \varepsilon), \bar{y}_{\mathrm{mi}}(x)) \qquad (29)$$

is assumed to have a quadratic surrogate for $l \geq 0$, where the following functions are defined for later use:

$$b_{\mathrm{mi}}(x, \varepsilon) \triangleq \bar{y}_{\mathrm{mi}}(x) / t_{\mathrm{mi}}(x, \varepsilon) \qquad (30)$$

$$t_{\mathrm{mi}}(x, \varepsilon) \triangleq \exp(-[A_m(\varepsilon)x]_i) + r_{\mathrm{mi}} / I_{\mathrm{mi}} \qquad (31)$$

$$r_{\mathrm{mi}}(x, \varepsilon) \triangleq b_{\mathrm{mi}}(x, \varepsilon) r_{\mathrm{mi}} / I_{\mathrm{mi}}. \qquad (32)$$

In other words, it is assumed that there exists a curvature function $c_{mi}(x, \epsilon)$ such that the following parabola is a surrogate for $g_{mi}$:

$$q_{\mathrm{mi}}(l, x, \varepsilon) = g_{\mathrm{mi}}([A_m(\varepsilon)x]_i, x, \varepsilon) + \qquad (33)$$
$$\dot{g}_{\mathrm{mi}}([A_m(\varepsilon)x]_i, x, \varepsilon)(l - [A_m(\varepsilon)x]_i) + \frac{1}{2}c_{\mathrm{mi}}(x, \varepsilon)(l - [A_m(\varepsilon)x]_i)^2,$$

where $$\dot{g}_{\mathrm{mi}}(l, x, \varepsilon) \triangleq \frac{\partial}{\partial l} g_{\mathrm{mi}}(l, x, \varepsilon).$$

In assuming that $q_{mi}$ is a surrogate for $g_{mi}$, it is meant that $c_{mi}$ is such that $$q_{mi}(l, x, \epsilon) \geq g_{mi}(l, x, \epsilon), \forall x \geq 0, \forall l \geq 0. \qquad (34)$$

The construction (33) provides the following two surrogate properties:

$$q_{\mathrm{mi}}(l, x, \varepsilon)|_{l=[A_m(\varepsilon)x]_i} = g_{\mathrm{mi}}([A_m(\varepsilon)x]_i, x, \varepsilon)$$
$$\dot{q}_{\mathrm{mi}}(l, x, \varepsilon)|_{l=[A_m(\varepsilon)x]_i} = \dot{g}_{\mathrm{mi}}([A_m(\varepsilon)x]_i, x, \varepsilon).$$

B.1 Existence of Convex Surrogates

The existence of a differentiable convex surrogate $h_{mi}$ satisfying (26) and (27) always holds when $\psi_{mi}$ is twice differentiable, which it will always be for physically plausible statistical models.

Let $\psi(y)$ be any twice differentiable function and define $$h(y, z) = \psi(z) + \dot{\psi}(z)(y - z) + \int_z^y (y - \tau) \max\{\ddot{\psi}(\tau), 0\} d\tau. \qquad (35)$$

This surrogate h is convex and (twice) differentiable and satisfies (26) and (27). The construction (35) may not be the optimal surrogate in terms of convergence rate, but it confuims that the third assumption above is unrestrictive.

Of course, if $\psi_{mi}$ is itself convex, such as in the Poisson case, then one simply takes $h_{mi}(y, \bullet) = \psi_{mi}(y)$.

B.2 Existence of Parabola Surrogates

To derive a specific algorithm for a particular negative log-likelihood $\psi_{mi}$ one will need to determine the $c_{mi}$ function in (33) by careful analysis. In the case of Poisson measurements, where $\psi_{mi}(y) = h_{mi}(y, \bullet) = y - y_{mi} \log y$, the optimal $c_{mi}$ function was shown to be:

$$c_{\mathrm{mi}}^{opt}(x, \varepsilon) \triangleq c_{opt}([A_m(\varepsilon)x]_i, y_{\mathrm{mi}}, b_{\mathrm{mi}}(x, \varepsilon), r_{\mathrm{mi}}(x, E)), \qquad (36)$$

where $$c_{opt}(l, y, b, r) = \begin{cases} \left[-2\frac{z(l, y, b, r)}{l^2}\right]_+, & l > 0 \\ [-\ddot{g}(l, y, b, r)]_+, & l = 0, \end{cases} \qquad (37)$$

where $$z(l, y, b, r) \triangleq g(0, y, b, r) - g(l, y, b, r) + \dot{g}(l, y, b, r)l \qquad (38)$$
$$g(l, y, b, r) = (be^{-l} + r) - y\log(be^{-l} + r)$$

$$\dot{g}(l, y, b, r) = \frac{\partial}{\partial l} g = \left[1 - \frac{y}{be^{-l} + r}\right](-1)be^{-l} \qquad (39)$$

$$\ddot{g}(l, y, b, r) = \frac{\partial^2}{\partial l^2} g = \left[1 - \frac{yr}{(be^{-l} + r)^2}\right] be^{-l}. \qquad (40)$$

By "optimal" is meant the choice the leads to the fastest convergence.

It was also shown that the curvature choice (37) is optimal not only for Poisson measurements, but also for a fairly broad fa$_{mi}$ly of negative log-likelihoods.

Alternatively, if $g_{mi}$ has bounded curvature, then one could use the upper bound on that curvature as the choice for $c_{mi}$. This approach was called "maximum curvature." It is the simplest choice, but is suboptimal in terms of convergence rate. To summarize, assuming existence of parabola surrogates should not unduly restrict the class of statistical models.

C. Likelihood Formulation

Under the above assumptions, including statistical independence of the transmission measurements, the negative log-likelihood corresponding to the above physical model has the form $$-L(x) \equiv \Psi(x) \triangleq \sum_{m=1}^{N_s} \sum_{i=1}^{N_d} \psi_{\mathrm{mi}}(\bar{y}_{\mathrm{mi}}(x)) \qquad (41)$$

for some scalar functions $\psi_{mi}$ that depend on the selected statistical model. Our goal is to estimate the coefficient vector x from the measurements $\{Y_{mi}\}$ by maximizing the log-likelihood or equivalent by finding a minimizer of the cost function $\Psi$ (or a regularized version thereof):

$$\hat{x}_{ML} \triangleq \underset{x}{\operatorname{argmin}} \Psi(x).$$

Optimization is restricted to the valid parameter space (i.e., including non-negativity constraints, etc.). Ignoring any constraints, in principle one could find a minimizer by zeroing the following partial derivatives of the cost function:

$$\frac{\partial}{\partial x_k}\Psi(x) = \sum_{m=1}^{N_s}\sum_{i=1}^{N_d}\dot{\psi}_{mi}(\bar{y}_{mi}(x))\frac{\partial}{\partial x_k}\bar{y}_{mi}(x) \qquad (42)$$

$$= \sum_{m=1}^{N_s}\sum_{i=1}^{N_d}\dot{\psi}_{mi}(\bar{y}_{mi}(x))\cdot$$

$$(-1)\int I_{mi}(\varepsilon)a_{mik}(\varepsilon)e^{-[A_m(\varepsilon)x]_i}d\varepsilon,$$

where $$\dot{\psi}_{mi}(y) \triangleq \frac{d}{dy}\psi_{mi}(y).$$

In general, there is no closed form solution to the set of $K_p$ equations (42), so iterative algorithms are required.

Although many algorithms have been proposed for the monoenergetic problem (8), none of those previously proposed algorithms is suitable for minimizing the cost function $\Psi(x)$ in the polyenergetic case. The greatest difficulty is the integral over energy in (24). Substituting a summation for this integral does not significantly simplify the problem. Further difficulties arise due to the nonlinearity of Beer's law in (1), and due to the nonquadratic form of typical choices for $\psi_{mi}$ (cf. (25)). In the next section, optimization transfer principles are applied to derive an iterative algorithm that monotonically decreases the cost function of each iteration. It should converge to a local minimizer, and should converge to the global minimizer if the cost function is unimodal. (The cost function is convex in the monoenergetic case under the Poisson model if the $r_{li}$'s are zero.) Global convergence needs further exa$_{mi}$nation. Many variations on this basic algorithm are possible. In particular, one could apply many general purpose minimization methods to minimize $\psi$, but most such methods would not provide monotonic decreases.

ML Algorithm

Since the cost function $\Psi(x)$ is difficult to minimize directly, optimization transfer principles are applied to develop an algorithm that monotonically decreases $\Psi(x)$ each iteration. (The extension to the penalized-likelihood case is straightforward, so the ML case is focused on here. The challenging part is the log-likelihood, not the penalty function.) To apply optimization transfer, at the nth iteration, one would like to find an easily-minimized surrogate function (the superscript "n" denotes an iteration index, not a power) $\phi(x,x^{(n)}) = \phi^{(n)}(x)$ that satisfies the majorizing conditions $$\phi^{(n)}(x^{(n)}) = \Psi(x^{(n)}) \qquad (43)$$

$$\phi^{(n)}(x) \geq \Psi(x). \qquad (44)$$

One then implements the following iteration:

$$x^{(n+1)} = \arg\min_x \phi^{(n)}(x). \qquad (45)$$

Optimization is restricted to the valid parameter space, such as $\{x \geq 0\}$. The conditions (43) and (44) ensure that an algorithm of the form (45) will monotonically decrease $\Psi$ each iteration: $\Psi(x^{(n+1)}) \geq \Psi(x^{(n)})$.

A suitable surrogate function is derived in this section by using several optimization transfer principles. DePierro's multiplicative convexity trick, parabola surrogates, and DePierro's additive convexity trick. The development partially parallels the derivation of a monotonic algorithm for SPECT transmission scans with overlapping beams. As described herein, the overlap is spectral rather than spatial. The final result of the derivation is the diagonally-scaled gradient descent algorithm (62) below.

A. Convex Surrogate

In general, $\Psi(x)$ will not be convex, so a convex surrogate is first formed to simplify minimization. Using the convex surrogate $h_{mi}$ described in (27), one defines $$h_{mi}^{(n)}(y) \triangleq h_{mi}(y, \bar{y}_{mi}(x^{(n)})), \qquad (46)$$

and then constructs the following surrogate function for $\Psi$:

$$\phi_0^{(n)}(x) \triangleq \sum_{m=1}^{N_s}\sum_{i=1}^{N_d} h_{mi}^{(n)}(\bar{y}_{mi}(x)). \qquad (47)$$

It follows from (26) and (27) that the surrogate $\phi_0^{(n)}$ satisfies the monotonicity conditions (43) and (44).

B. Surrogate Based on Multiplicative Convexity Trick

Typically, $\phi_0^{(n)}$ is also difficult to minimize directly, so the next step is to further simplify by deriving a surrogate function using DePierro's multiplicative convexity trick, generalized from summations to integrals. One first rewrites $\bar{y}_{mi}$ in (24) as follows:

$$\bar{y}_{mi}(x) = \int I_{mi}(\varepsilon)t_{mi}(x,\varepsilon)d\varepsilon \qquad (48)$$

$$= \int \left[\frac{I_{mi}(\varepsilon)}{b_{mi}^{(n)}(\varepsilon)}\right] t_{mi}(x,\varepsilon)b_{mi}^{(n)}(\varepsilon)d\varepsilon,$$

where $t_{mi}$ and $b_{mi}$ were defined in (31) and (30), and we define $$t_{mi}^{(n)}(\varepsilon) \triangleq t_{mi}(x^{(n)},\varepsilon) \qquad (49)$$

$$b_{mi}^{(n)}(\varepsilon) \triangleq b_{mi}(x^{(n)},\varepsilon).$$

(Many $b_{mi}^{(n)}(\varepsilon)$'s would satisfy (50) and hence (44), but only the choice (49) leads to (43)). The key feature of the equality (48) is that the terms in the brackets are nonnegative and integrate to unity, enabling use of the convexity inequality (i.e., Jensen's inequality). If h is any function that is convex on $(0,\infty)$, then $$h(\bar{y}_{mi}(x)) = h\left(\int \left[\frac{I_{mi}(\varepsilon)}{b_{mi}^{(n)}(\varepsilon)}\right] t_{mi}(x,\varepsilon)b_{mi}^{(n)}(\varepsilon)d\varepsilon\right) \qquad (50)$$

$$\leq \int \frac{I_{mi}(\varepsilon)}{b_{mi}^{(n)}(\varepsilon)} h(t_{mi}(x,\varepsilon)b_{mi}^{(n)}(\varepsilon))d\varepsilon.$$

Since $h_{mi}^{(n)}$ in (47) is convex by assumption, one can apply the above trick to it, thereby deriving our next surrogate function for the cost function as follows:

$$\phi_0^{(n)}(x) = \sum_{m=1}^{N_s}\sum_{i=1}^{N_d} h_{mi}^{(n)}(\bar{y}_{mi}(x)) \qquad (51)$$

$$\leq \int \sum_{m=1}^{N_s}\sum_{i=1}^{N_d} \frac{I_{mi}(\varepsilon)}{b_{mi}^{(n)}(\varepsilon)} h_{mi}^{(n)}(t_{mi}(x,\varepsilon)b_{mi}^{(n)}(\varepsilon))d\varepsilon$$

-continued $$\stackrel{\Delta}{=} \phi_1^{(n)}(x).$$

Using the equality $t_{mi}(x^{(n)},\epsilon)b_{mi}^{(n)}(\epsilon)=\bar{y}_{mi}(x^{(n)})$, one can verify that $\phi_1^{(n)}$ is a valid surrogate that satisfies the monotonicity conditions (43) and (44).

As a sanity check, in the case of monoenergetic sources we have $I_{mi}(\epsilon)=I_m\delta(\epsilon-\epsilon_m)$, for which $t_{mi}(x,\epsilon_m)=\bar{y}_{mi}(x)/I_m$ and hence $b_{mi}^{(n)}(\epsilon)=I_m$. In this case $\phi_1^{(n)}(x)=\phi_0^{(n)}(x)$. So the monoenergetic problem is a degenerate special case of the algorithm derived hereafter.

The surrogate function $\phi_1^{(n)}$ "brings the integral over $\epsilon$ to the outside," simplifying the optimization. Nevertheless, $\phi_1^{(n)}$ is difficult to minimize directly, so we find a paraboloidal surrogate function for it.

C. Paraboloidal Surrogate

The next surrogate is based on paraboloids. For brevity, define $$r_{mi}^{(n)}(\varepsilon) \stackrel{\Delta}{=} r_{mi}(x^{(n)}, \varepsilon),$$

where $r_{mi}$ was defined in (32). Using (29)–(31) we have:

$$h_{mi}^{(n)}(t_{mi}(x,\varepsilon)b_{mi}^{(n)}(\varepsilon)) \quad (52)$$
$$= h_{mi}(b_{mi}^{(n)}(\varepsilon)\exp(-[A_m(\varepsilon)x]_i) + r_{mi}^{(n)}(\varepsilon), \bar{y}_{mi}(x^{(n)}))$$
$$= g_{mi}^{(n)}([A_m(\varepsilon)x]_i, \varepsilon),$$

where $g_{mi}$ was defined in (29) and $$g_{mi}^{(n)}(l, \varepsilon) \stackrel{\Delta}{=} g_{mi}(l, x^{(n)}, \varepsilon).$$

The surrogate $\phi_1^{(n)}$ is rewritten in (51) as follows:

$$\phi_1^{(n)}(x) = \sum_{m=1}^{N_s}\sum_{i=1}^{N_d}\int \frac{I_{mi}(\varepsilon)}{b_{mi}^{(n)}(\varepsilon)} g_{mi}^{(n)}([A_m(\varepsilon)x]_i, \varepsilon)d\varepsilon. \quad (53)$$

As described hereinabove, it is assumed that $g_{mi}$ has a parabola surrogate $q_{mi}$ of the form (33), so these parabolas are combined using (53) to form a paraboloidal surrogate:

$$\phi_1^{(n)}(x) \leq \sum_{m=1}^{N_s}\sum_{i=1}^{N_d}\int \frac{I_{mi}(\varepsilon)}{b_{mi}^{(n)}(\varepsilon)} q_{mi}^{(n)}([A_m(\varepsilon)x]_i, \varepsilon)d\varepsilon \quad (54)$$
$$\stackrel{\Delta}{=} \phi_2^{(n)}(x),$$

where $$q_{mi}^{(n)}(l, \varepsilon) \stackrel{\Delta}{=} q_{mi}(l, x^{(n)}, \varepsilon).$$

Using (33) and (34), one canverify that $\phi_2^{(n)}$ is a valid surrogate that satisfies the monotonicity conditions (43) and (44).

$\phi_2^{(n)}$ is a quadratic form, so one could apply any of a variety of algorithms to minimize it per (45). Two choices are focused on. One choice is coordinate descent, which is known to converge rapidly. However, coordinate descent works best when the $a_{mik}(\epsilon)$'s are precomputed and stored. This storage may require more memory than current workstations allow for X-ray CT sized problems. The second choice is to find yet another surrogate, this time a separable function for which the minimization step (45) becomes trivial.

D. Coordinate Descent

Implementing a coordinate descent algorithm to minimize the paraboloidal surrogate $\phi^{2(n)}$ would require the following partial derivatives:

$$\frac{\partial}{\partial x_k}\phi_2^{(n)}(x) = \sum_{m=1}^{N_s}\sum_{i=1}^{N_d}\int a_{mik}(\varepsilon)\frac{I_{mi}(\varepsilon)}{b_{mi}^{(n)}(\varepsilon)}\dot{q}_{mi}^{(n)}([A_m(\varepsilon)x]_i, \varepsilon)d\varepsilon \quad (55)$$
$$= \sum_{m=1}^{N_s}\sum_{i=1}^{N_d}\int a_{mik}(\varepsilon)\frac{I_{mi}(\varepsilon)}{b_{mi}^{(n)}(\varepsilon)}[\dot{q}_{mi}^{(n)}(l_{mi}^{(n)}(\varepsilon), \varepsilon) +$$
$$\ddot{c}_{mi}^{(n)}(\varepsilon)([A_m(\varepsilon)x]_i - l_{mi}^{(n)}(\varepsilon))]d\varepsilon,$$

where we define $$l_{mi}^{(n)}(\varepsilon) \stackrel{\Delta}{=} [A_m(\varepsilon)x^{(n)}]_i \quad \text{and} \quad c_{mi}^{(n)}(\varepsilon) \stackrel{\Delta}{=} c_{mi}(x^{(n)}, \varepsilon). \quad (56)$$

Applying the chain rule to (29) yields:

$$\dot{g}_{mi}^{(n)}(l, \epsilon) = \dot{h}_{mi}^{(n)}(b_{mi}^{(n)}(\epsilon)e^{-l} + r_{mi}^{(n)}(\epsilon))b_{mi}^{(n)}(\epsilon)(-1)e^{-l},$$

so using (28):

$$\dot{g}_{mi}^{(n)}(l, \varepsilon)|_{l=l_{mi}^{(n)}(\varepsilon)} = \dot{h}_{mi}\left(b_{mi}^{(n)}(\varepsilon)e^{-l_{mi}^{(n)}(\varepsilon)} + r_{mi}^{(n)}(\varepsilon)\right)b_{mi}^{(n)}(\varepsilon)(-1)e^{-l_{mi}^{(n)}(\varepsilon)}$$
$$= \dot{\psi}_{mi}(\bar{y}_{mi}(x^{(n)}))b_{mi}^{(n)}(\varepsilon)(-1)e^{-l_{mi}^{(n)}(\varepsilon)},$$

and hence $$\frac{\partial}{\partial x_k}\phi_2^{(n)}(x) = \sum_{m=1}^{N_s}\sum_{i=1}^{N_d}\int a_{mik}(\varepsilon)\frac{I_{mi}(\varepsilon)}{b_{mi}^{(n)}(\varepsilon)}\dot{g}_{mi}^{(n)}(l_{mi}^{(n)}(\varepsilon), \varepsilon)d\varepsilon +$$
$$\sum_{m=1}^{N_s}\sum_{i=1}^{N_d}\int a_{mik}(\varepsilon)w_{mi}^{(n)}(\varepsilon)[A_m(\varepsilon)(x-x^{(n)})]_i d\varepsilon$$
$$= \sum_{m=1}^{N_s}\sum_{i=1}^{N_d}\dot{\psi}_{mi}(\bar{y}_{mi}(x^{(n)}))\int a_{mik}(\varepsilon)I_{mi}(\varepsilon)(-1)e^{-[A_m(\varepsilon)x^{(n)}]_i}d\varepsilon +$$
$$\sum_{m=1}^{N_s}\sum_{i=1}^{N_d}\int a_{mik}(\varepsilon)w_{mi}^{(n)}(\varepsilon)[A_m(\varepsilon)(x-x^{(n)})]_i$$
$$= \frac{\partial}{\partial x_k}\Psi(x)\bigg|_{x=x^{(n)}} +$$
$$\sum_{m=1}^{N_s}\sum_{i=1}^{N_d}\sum_{j=1}^{N_p}\int a_{mik}(\varepsilon)a_{mij}(\varepsilon)w_{mi}^{(n)}(\varepsilon)d\varepsilon(x_j - x_j^{(n)}),$$

using (42), where $$w_{mi}^{(n)}(\varepsilon) \stackrel{\Delta}{=} \frac{I_{mi}(\varepsilon)}{b_{mi}^{(n)}(\varepsilon)}c_{mi}^{(n)}(\varepsilon).$$

This "matched derivative" property is inherent to optimization transfer methods.

For the second partial derivatives, using (54) and (56):

$$\frac{\partial^2}{\partial x_k \partial x_j} \phi_2^{(n)}(x) = \sum_{m=1}^{N_s} \sum_{i=1}^{N_d} \int a_{mik}(\varepsilon) a_{mij}(\varepsilon) w_{mi}^{(n)}(\varepsilon) d\varepsilon,$$

In particular, $$\frac{\partial^2}{\partial x_k^2} \phi_2^{(n)}(x) = \sum_{m=1}^{N_s} \sum_{i=1}^{N_d} \int [a_{mik}(\varepsilon)]^2 w_{mi}^{(n)}(\varepsilon) d\varepsilon. \quad (57)$$

Combining (56) and (57) leads directly to a coordinate-descent algorithm with inner update:

$$x_k^{(n+1)} = \left[ x_k^{(n)} - \frac{\left.\frac{\partial}{\partial x_k} \Psi(x)\right|_{x = \left(x_1^{(n+1)}, \ldots, x_{k-1}^{(n+1)}, x_k^{(n)}, \ldots, x_{K_b}^{(n)}\right)}}{\frac{\partial^2}{\partial x_k^2} \phi_2^{(n)}(\cdot)} \right]_+,$$

where $[x]_+$ enforces the non-negativity constraint.

E. Surrogate Based on Additive Convexity Trick

The surrogate function $\phi_2^{(n)}$ is a non-separable quadratic function of x (a paraboloid). Non-separability is fine for coordinate descent, but inconvenient for simultaneous update algorithms. To derive a simple simultaneous update algorithm (fully parallelizable and suitable for ordered-subsets implementation), we find next a separable paraboloid surrogate by applying DePierro's additive convexity trick. The key is the following equality (an additive analog of the multiplicative form (48)):

$$[A_m(\varepsilon) x]_i = \sum_{k=1}^{K_b} a_{mik}(\varepsilon) x_k = \sum_{k=1}^{K_b} \pi_{mik}(\varepsilon) u_{mik}^{(n)}(x_k, \varepsilon)$$

where $$u_{mik}^{(n)}(x_k, \varepsilon) \triangleq \frac{a_{mik}(\varepsilon)}{\pi_{mik}(\varepsilon)} (x_k - x_k^{(n)}) + [A_m(\varepsilon) x^{(n)}]_i,$$

provided the $\pi_{mik}(\epsilon)$'s are non-negative and are zero only when $a_{mik}(\epsilon)$ is zero, and that $$\sum_{k=1}^{K_b} \pi_{mik}(\varepsilon) = 1.$$

Since $q_{mi}^{(n)}(1, \epsilon)$ is a convex function, by the convexity inequality (cf. (50)) we have:

$$q_{mi}^{(n)}([A_m(\varepsilon) x]_i,$$

$$\varepsilon = q_{mi}^{(n)}\left(\sum_{k=1}^{K_b} \pi_{mik}(\varepsilon) u_{mik}^{(n)}(x_k, \varepsilon), \varepsilon\right) \leq \sum_{k=1}^{K_b} \pi_{mik}(\varepsilon) q_{mi}^{(n)}(u_{mik}^{(n)}(x_k, \varepsilon), \varepsilon).$$

This exchange "brings out the sum over k." Combining (54) leads to the following final surrogate function:

$$\phi_3^{(n)}(x) \triangleq \sum_{m=1}^{N_s} \sum_{i=1}^{N_d} \int \frac{I_{mi}(\varepsilon)}{b_{mi}^{(n)}(\varepsilon)} \left[ \sum_{k=1}^{K_b} \pi_{mik}(\varepsilon) q_{mi}^{(n)}(u_{mik}^{(n)}(x_k, \varepsilon), \varepsilon) \right] d\varepsilon. \quad (58)$$

The surrogate $\phi_3^{(n)}$ is convenient because it is separable:

$$\phi_3^{(n)}(x) = \sum_{k=1}^{K_b} \phi_{3,k}^{(n)}(x_k)$$

where $$\phi_{3,k}^{(n)}(x_k) \triangleq \sum_{m=1}^{N_s} \sum_{i=1}^{N_d} \int \frac{I_{mi}(\varepsilon)}{b_{mi}^{(n)}(\varepsilon)} \pi_{mik}(\varepsilon) q_{mi}^{(n)}(u_{mik}^{(n)}(x_k, \varepsilon), \varepsilon) d\varepsilon. \quad (59)$$

Combining separability with (45) leads to the following fully parallelizable algorithm:

$$X_k^{(n+1)} = \arg\min_{x_k} \phi_{3,k}^{(n)}(x_k), \quad k = 1, \ldots, K_b.$$

As always, one must consider any constraints such as non-negativity. Since $\phi_{3,k}^{(n)}$ is a quadratic function, it is trivial to minimize as follows:

$$x_k^{(n+1)} = \left[ x_k^{(n)} - \frac{\left.\frac{\partial}{\partial x_k} \phi_{3,k}^{(n)}(x_k)\right|_{x_k = x_k^{(n)}}}{\left.\frac{\partial^2}{\partial x_k^2} \phi_{3,k}^{(n)}(x_k)\right|_{x_k = x_k^{(n)}}} \right]_+. \quad (60)$$

From (59) and (55), the partial derivatives needed are:

$$\left.\frac{\partial}{\partial x_k} \phi_{3,k}^{(n)}(x_k)\right|_{x_k = x_k^{(n)}} = \sum_{m=1}^{N_s} \sum_{i=1}^{N_d} \int \frac{I_{mi}(\varepsilon)}{b_{mi}^{(n)}(\varepsilon)} a_{mik}(\varepsilon) \dot{q}_{mi}^{(n)}([A_m(\varepsilon) x^{(n)}]_i, \varepsilon) d\varepsilon$$

$$= \left.\frac{\partial}{\partial x_k} \Psi(x)\right|_{x = x^{(n)}}$$

and $$\left.\frac{\partial^2}{\partial x_k^2} \phi_{3,k}^{(n)}(x_k)\right|_{x_k = x_k^{(n)}} = \sum_{m=1}^{N_s} \sum_{i=1}^{N_d} \int \frac{(a_{mik}(\varepsilon))^2}{\pi_{mik}(\varepsilon)} w_{mi}^{(n)}(\varepsilon) d\varepsilon.$$

A useful choice for the $\pi_{mik}(\epsilon)$'s is:

$$\pi_{mik}(\varepsilon) = \frac{a_{mik}(\varepsilon)}{a_{mi}(\varepsilon)},$$

where $$a_{mi}(\varepsilon) \triangleq \sum_{k=1}^{K_b} a_{mik}(\varepsilon). \quad (61)$$

Substituting into (60) yields the following algorithm:

$$x_k^{(n+1)} = \left[ x_k^{(n)} - \frac{\frac{\partial}{\partial x_k}\Psi(x)\big|_{x=x^{(n)}}}{d_k^{(n)}} \right], \quad (62)$$

for $k=1, \ldots, K_p$, wherein $$d_k^{(n)} \triangleq \sum_{m=1}^{N_s} \sum_{i=1}^{N_d} \int a_{mik}(\varepsilon) a_{mi}(\varepsilon) w_{mi}^{(n)}(\varepsilon) d\varepsilon, \quad (63)$$

and $$\frac{\partial}{\partial x_k}\Psi(x^{(n)})$$

was defined in (42). This is a diagonally-scaled gradient-descent algorithm that is guaranteed to monotonically decrease the cost function each iteration.

Both the first derivatives (42) and the denominators $\{d_k^{(n)}\}$ require integrals over energy. These integrals can be computed by standard discrete approximations, to whatever accuracy the source spectrum and material properties are known. This is fundamentally different than making linear or polynomial approximations in the model at the outset.

To make a more practical algorithm, it would probably be reasonable to adopt the "precomputed fast denominator" idea and to apply the ordered subsets principles. Applying these principles alone would cause a loss of guaranteed monotonicity, but have proven to be useful in practice. By applying suitable relaxation, one could even guarantee convergence if the cost function were convex.

FIG. 1a shows a flow chart of the method or algorithm of the present invention. Initially, two or more raw sinograms are obtained such as from a detector of FIG. 1b. Calibration data for the source spectra are also provided.

Component line integrals and error covariances are estimated utilizing the raw sinograms and the calibration data.

FBP reconstruction of component images is then performed utilizing the component line integrals. Then, optionally, component images are created utilizing iterative WLS reconstruction utilizing the component line integrals, component error covariances and the component images.

Then, either the component images obtained by FBP reconstruction or the component images constructed by iterative WLS are chosen to reproject in the next step which reprojects the chosen components to estimate line integrals.

Then, measurement means and gradients are computed.

The measurement means and gradients are utilized by a backprojection process to compute the cost function gradient.

The component images are updated using correction factors. Component constraints are applied such as non-negativity.

The number of iterations is checked against a predetermined number or other criteria related to the component images and data are considered, and if the iterative part of the method is complete, then, the final component images are displayed and/or analyzed. If not done, then the iterative part of the method is re-entered at the choosing step.

Alternatively, after reconstruction of the component images is performed by the iterative WLS reconstruction step, the component images may be displayed and/or analyzed as indicated by the dashed line in FIG. 1a.

Figure 1B:
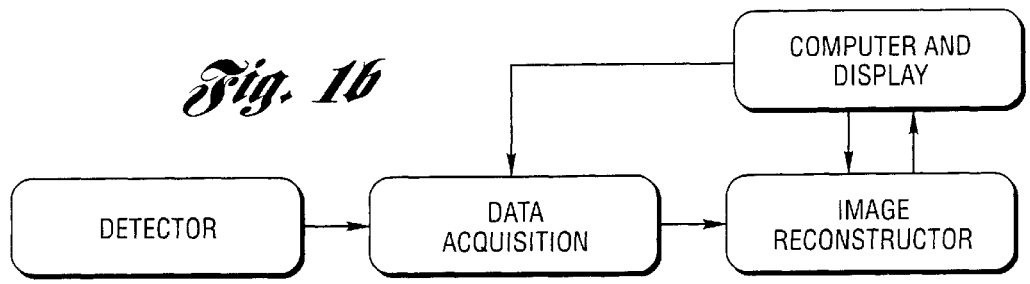
FIG. 1b is a schematic block diagram of a reconstruction apparatus of the present invention for use in a basic CT subsystem.

FIG. 1b is a simplified schematic block diagram showing how an image reconstructor of the present invention interacts with the subsystem of a simple CT subsystem to perform the method of FIG. 1a.

F. ML Dual-Energ Case

Perhaps the most common application of this algorithm will be to dual-energy X-ray CT reconstruction with a two-component separable basis of the following form (cf. (3)):

$$\chi_k(\vec{x}, \varepsilon) = \begin{cases} \beta_1(\varepsilon) b_k(\vec{x}), & k = 1, \ldots, N_p \\ \beta_2(\varepsilon) b_{k-N_p}(\vec{x}), & k = N_p + 1, \ldots, 2N_p, \end{cases}$$

with $K=2N_p$, for some spatial basis $\{b_j(\vec{x})\}_{j=1}^{N_p}$ such as pixels, where $\beta_1(\varepsilon)$ and $\beta_2(\varepsilon)$ denote the spectral properties of the two basis materials. For simplicity, also assume that the measured ray configuration is the same for both incident spectra, i.e., $L_{mi} = L_i$ for $m=1,2$. In this case, $$a_{mik}(\varepsilon) = \begin{cases} \beta_1(\varepsilon) a_{ik}, & k = 1, \ldots, N_p \\ \beta_2(\varepsilon) a_{i,k-N_p}, & k = N_p + 1, \ldots, 2N_p, \end{cases}$$

where $a_{ij}$ was defined in (9). In other words, $$A_m(\varepsilon)x = \beta_1(\varepsilon) A x_1 + \beta_2(\varepsilon) A x_2, \quad (64)$$

where $x=(x_1, x_2)$ and where $x_1$ and $x_2$ represent the basis coefficients (voxel values) for the two component images. This expression is independent of m. Furthermore, from (61)

$$a_{mi}(\varepsilon) = [\beta_1(\varepsilon) + \beta_2(\varepsilon)] a_i,$$

where $$a_i \triangleq \sum_{j=1}^{N_p} a_{ij}.$$

With these simplifications, the measurement mean model (24) becomes $$\bar{y}_{mi}(x) = I_{mi} e^{-f_{im}([Ax_1]_i,[Ax_2]_i)} + r_{mi} \quad (65)$$

where $f_{im}$ and $I_{mi}$ were defined above.

Given incident source spectra $I_{mi}(\varepsilon)$, one can precompute and tabulate $f_{im}$ for $m=1,2$. Since $f_{im}$ is nearly linear, a modest table combined with bilinear interpolation is effective. (For monoenergetic sources, $f_{im}$ would be exactly linear.) Alternatively, a polynomial approximation togf can be used.

The algorithm (62) also requires the partial derivatives of the cost function. Using (64), the partial derivatives (42) simplify to $$\frac{\partial}{\partial x_{lj}}\Psi(x) = \quad (66)$$

$$\sum_{i=1}^{N_d} a_{ij} \left[ \sum_{m=1}^{N_i} \dot{\psi}_{mi}(\bar{y}_{mi}(x)) \tilde{G}_{iml}([Ax_1]_i, [Ax_2]_i)(\bar{y}_{mi}(x) - r_{mi}) \right],$$

for $j=1, \ldots, N_p$ and $l=1,2$, where $x_{lj}$ denotes the jth component of $x_l$, and where $\tilde{G}_{iml}(s_1, s_2)$ denotes the derivative of $f_{im}(s_1, s_2)$ with respect to $s_1$. Thus, the algorithm (62) becomes:

$$x_{lj}^{(n+1)} = \left[ x_{lj}^{(n)} - \frac{\frac{\partial}{\partial x_{lj}} \Psi(x^{(n)})}{d_{lj}^{(n)}} \right]_+, \quad (67)$$

for $j=1, \ldots, N_p$, $l=1,2$, where $$\frac{\partial}{\partial x_{lj}} \Psi$$

defined in (66), and from (63)

$$d_{lj}^{(n)} = \sum_{i=1}^{N_d} a_{ij} a_i \sum_{m=1}^{N_s} \int \tilde{\beta}_l(\varepsilon) w_{mi}^{(n)}(\varepsilon) d\varepsilon. \quad (68)$$

where $$\tilde{\beta}_l(\varepsilon) \triangleq \beta_l(\varepsilon)(\beta_1(\varepsilon) + \beta_2(\varepsilon)).$$

Since the integral in (68) depends on the current iterate $x^{(n)}$, it cannot be precomputed and tabulated. One integral per ray is needed, followed by one backprojection per material component. Thus, the guarantee of intrinsic monotonicity requires roughly a 50% increase in computation per iteration over an algorithm in which the $d_{ij}$'s are precomputed. In similar previous studies, it has been observed that one can use precomputed approximations to the $d_{lj}^{(n)}$'s yet preserve monotonicity almost always. This observation motivates the following hybrid approach: we first use precomputed $d_{lj}^{(n)}$'s each iteration, and then check the cost function to verify that it decreased. If not, then the update is recomputed using the $d_{lj}^{(n)}$'s that intrinsically guarantee a monotone decrease. Only very rarely is this recomputation required, so the resulting "hybrid" method is fast and practical yet also guaranteed to be monotone. When speed is considered more important than monotonicity, one can also easily apply ordered subsets to (67) by downsampling the sums over "i" in the derivative expressions.

G. Precomputed Curvatures

To reduce computation per iteration (at the price of losing the monotonicity guarantee), precomputed values may be used for the denominators $d_{ij}$. Observe that $c_{mi}$ is the curvature of $q_{mi}$ in (33), which is a parabola surrogate for $g_{mi}$ in (29). A reasonable approximation for $c_{mi}^{(n)}(\varepsilon)$ is to use the curvature $g_{mi}^{(n)}$ at its minimizer, i.e., $$c_{mi}^{(n)}(\varepsilon) \approx \ddot{g}_{mi}(l, x^{(n)}, \varepsilon)|_{l=\arg\min g_{mi}^{(n)}(l,\varepsilon)},$$

where $$\ddot{g}_{mi}(l, x, \varepsilon) \triangleq \frac{\partial^2}{\partial l^2} g_{mi}(l, x, \varepsilon).$$

From (29), for $P$ near the minimizer of $g_{mi}$:

$$\ddot{g}_{mi}(l,x,\varepsilon) \approx [-b_{mi}(x,\varepsilon)e^{-l}]_2 \dot{h}_{mi}(b_{mi}(x,\varepsilon)e^{-l} + r_{mi}(x,\varepsilon),x,\varepsilon).$$

The minimizer of $\psi_{mi}(y)$ and $h_{mi}(y, \bar{y}_{mi}(x^{(n)}))$ should be approximately where $y=y_{mi}$. (This holds exactly for the Poisson noise model.) So the minimizer of $g_{mi}^{(n)}$ should be approximately where $b_{mi}(x,\varepsilon)e^{-l} + r_{mi}(x,\varepsilon) = y_{mi}$. If $\psi_{mi}$ is nearly convex, then $h_{mi}$ and $\psi_{mi}$ should have approximately the same curvatures. Combining these heuristics with the assumption that $r_{mi}$ is neglible yields the approximation $$c_{mi}^{(n)}(\varepsilon) \approx y_{mi}^2 \ddot{\psi}_{mi}(y_{mi})$$

If $\psi_{mi}$ corresponds a statistical model that is approximately Poisson, then $\ddot{\psi}_{mi}(y_{mi}) \approx 1/y_{mi}$. Thus, we use the approximation $c_{mi}^{(n)}(\varepsilon) \approx y_{mi}$ hereafter, which we substitute into (68). To further simplify, we replace the $\beta_l(\varepsilon)$ values in (68) by their values at the effective energy of the mth incident spectrum:

$$\bar{\varepsilon}_m \triangleq \frac{\int \varepsilon I_{mi}(\varepsilon) d\varepsilon}{\int I_{mi}(\varepsilon) d\varepsilon}, \quad m = 1, 2, \quad (69)$$

yielding the approximation $$\int \tilde{\beta}_l(\varepsilon) \frac{I_{mi}(\varepsilon)}{b_{mi}^{(n)}(\varepsilon)} d\varepsilon \approx \tilde{\beta}_l(\bar{\varepsilon}_m) \int \frac{I_{mi}(\varepsilon)}{b_{mi}^{(n)}(\varepsilon)} d\varepsilon = \tilde{\beta}_l(\bar{\varepsilon}_m),$$

using (30). Thus, the final precomputed approximation to $d_{lj}^{(n)}$ is $$d_{lj} \triangleq \sum_{i=1}^{N_d} a_{ij} a_i \sum_{m=1}^{N_s} y_{mi} \tilde{\beta}_l(\bar{\varepsilon}_m). \quad (70)$$

Precomputing (70) requires one object-independent forward projection (to compute the $a_i$'s), and two measurement-dependent backprojections (one for each l).

H. Examining $f_{im}$ Via a Linearizing Transformation

Since $$\frac{\partial}{\partial s_l} f_{im}(0, 0) = \bar{\beta}_{ml},$$

we define $$\begin{bmatrix} F_{1i}^* \\ F_{2i}^* \end{bmatrix} = \begin{bmatrix} \bar{\beta}_{11} & \bar{\beta}_{12} \\ \bar{\beta}_{21} & \bar{\beta}_{22} \end{bmatrix}^{-1} \begin{bmatrix} F_{1i} \\ F_{2i} \end{bmatrix}. \quad (71)$$

The effect of this transformation is that $$\frac{\partial}{\partial s_l} F_{mi}^*(0, 0) = 1_{l=m},$$

where 1 denotes the indicator function.

Results

A. Computer Simulation

To evaluate the feasibility of the proposed approach, a computer simulation of dual-energy polyenergetic CT scans was performed. Both the conventional dual-energy FBP reconstruction method, the proposed polyenergetic WLS method and the proposed ML reconstruction method were applied to those simulated measurements.

FIGS. 2a–2b show the source spectra for the two simulated source voltages (80 kVp and 140 kVp). The dashed lines in the Figures show the effective energies of these spectra, as defined by Equation (69).

The separable parameterization of Equation (21) was used. FIG. 3 shows the mass attenuation coefficients $\beta_l(\varepsilon)$ of bone mineral and soft tissue from NIST web pages:

http://physics.nist.gov/PhysRefData/XrayMassCoef/ComTab/tissue.html.

Figures 4A, 4B:
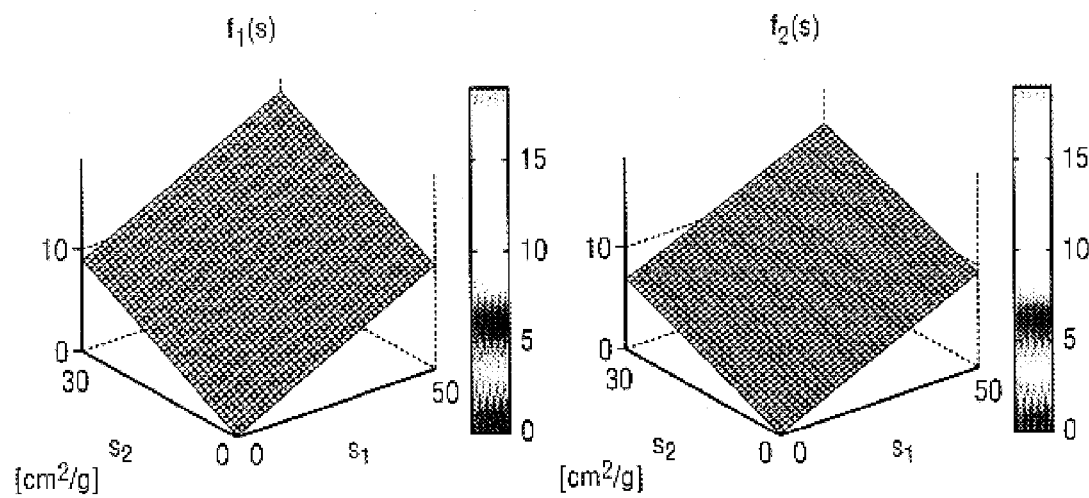
FIGS. 4a and 4b are 3D graphs of functions $f_{im}$ in Equation (11) corresponding to FIG. 2 and FIG. 3; the units of $s_1$ are $[cm^2/g]$.

FIGS. 4a and 4b show the function $f_{im}$ defined in (11). These functions look to be nearly linear, but they are not quite linear due to beam hardening.

Figure 5:
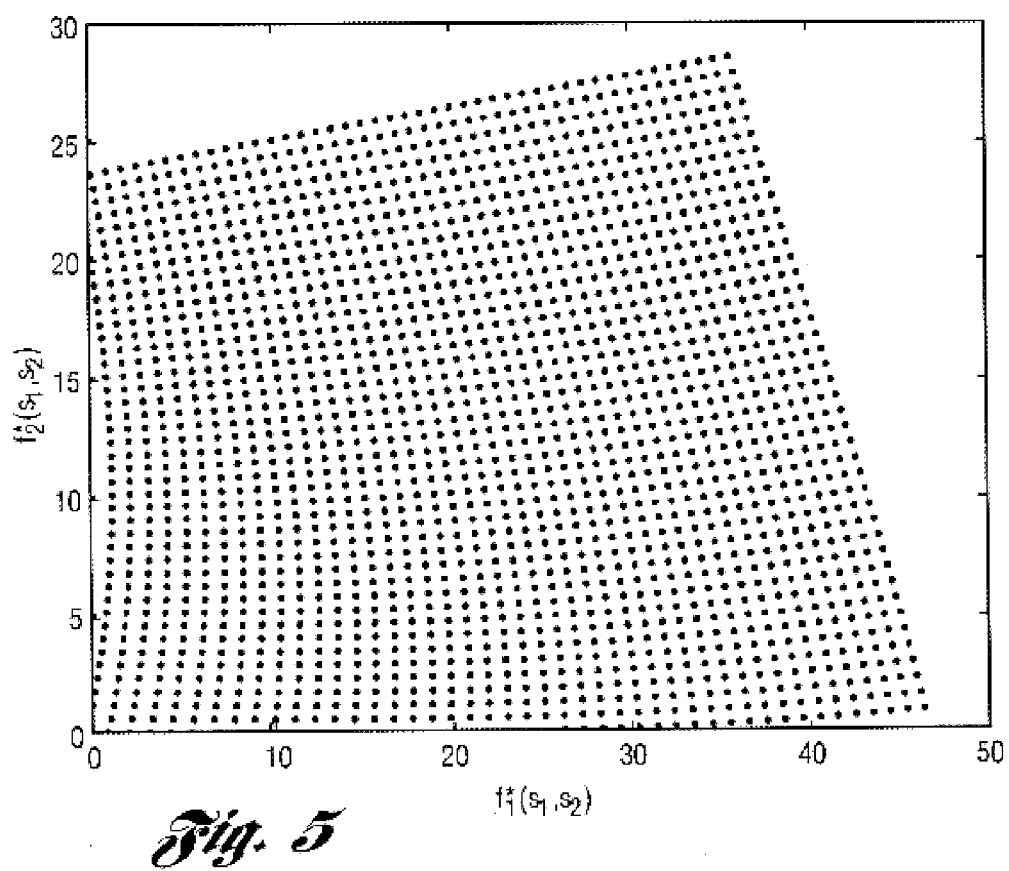
FIG. 5 is a scatter plot of $(F_1^*(s_1,s_2),F_2^*(s_1,s_2))$ pairs of Equation (71) for uniformly-spaced $(s_1,s_2)$ pairs; for a monoenergetic source these points would lie on a uniform grid; the nonlinearities are due to beam hardening effects.
Figures 6A, 6B, 6C, 6D:
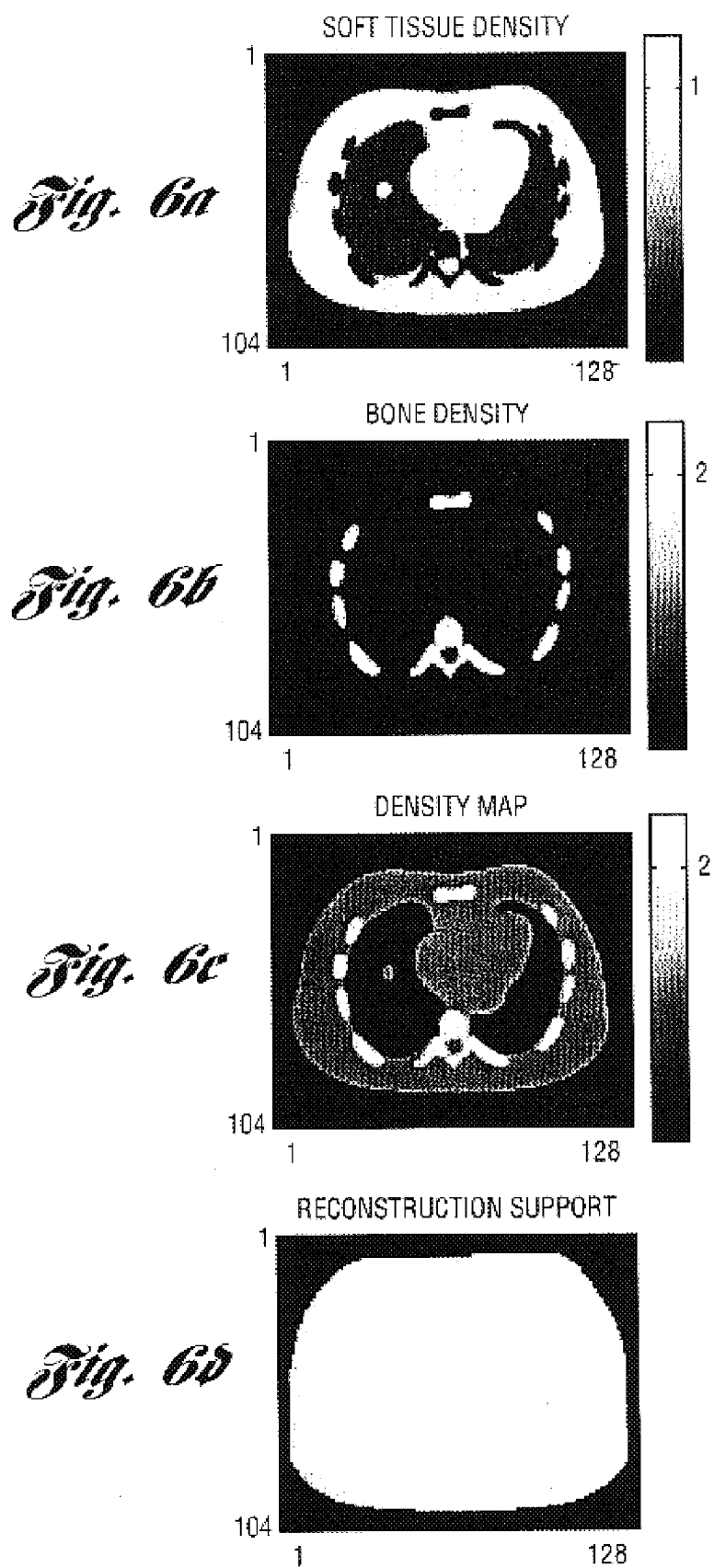
FIGS. 6a–6d illustrate a true object $x^{true}$ used in computer simulation.

FIG. 5 shows the linearized form (71) for uniform samples in $s_1$ and $S_2$. Near zero the values are nearly uniform (due to the Jacobian) but away from zero there are nonlinearities due to beam hardening.

FIGS. 6a–6d show the object $x^{true}$ used in the computer simulation. The units of x are density (g/cm$^3$) and were assigned to 1.0 for soft tissue, 0.2 for lungs, 1.9 for spine, and 2.0 for ribs. The lungs and soft tissue had the "soft tissue" characteristics shown in FIG. 3, and the spine and ribs had the "bone" characteristics of FIG. 3. The images were 128×104 and the pixel size was 0.32 cm.

We simulated dual-energy measurements $\bar{y}_{mi}$ using (24) and the spectra shown in FIGS. 2a and 2b. The sinograms 140 radial samples (parallel beam geometry with 0.32 cm sample spacing) and 128 angles over 180°. To the noiseless sinograms $\bar{y}_{mi}$ we added pseudo-random Poisson distributed noise corresponding to a total of 47M recorded photons (chosen arbitrarily to represent a moderately low SNR case where FBP yields noticeable streaks). FIGS. 7a and 7b show the simulated sinograms $Y_{mi}$.

We first show the results of conventional dual-energy tomographic reconstruction. FIGS. 8a and 8b show the estimates $\hat{f}^{im}$ described in (14) as computed from the noisy dual-energy sinograms, using a small amount of radial smoothing to help control noise. FIGS. 9a–9f show the estimates $\hat{s}_i$ described in (17) as computed from the $\hat{f}_{im}$'s. FIGS. 9a–9f also show the error sinograms. There is substantial error because the inversion in (17) is a noise-amplifying step due to the similarities between the two spectra in FIGS. 2a and 2b and the similarities of the mass attenuation coefficients in FIG. 3.

FIGS. 10a–10f show ramp-filtered FBP reconstructions of the soft-tissue and bone components from the $\hat{S}_i$'S shown in FIGS. 10a–10f. FIGS. 10a–10f also show the error images. Substantial noise propagates from the $\hat{S}$'s into the FBP images.

FIGS. 11a–11f show PL dual-energy reconstruction of soft tissue and bone components. The density units are i/cm.

FIGS. 10a–10f and 11a–11f illustrate the current tradeoff that faces X-ray CT imaging. Ordinary single-energy methods are inaccurate, whereas FBP-based dual-energy methods are unacceptably noisy.

Although the algorithm description in the preceding sections did not include regularization, it is straightforward to include regularization in this algorithm. A penalized-likelihood extension of the ML dual-energy method was implemented. In our implementation, we used pairwise pixel differences with a Huber potential function and a second-order neighborhood for the regularizing penalty function. The strength parameter was modulated to help provide resolution unifor$_{mi}$ty (away from object boundaries). Many other regularization methods could be used instead.

FIG. 12 shows the cost function changes $\Psi(x^{(n)})-\Psi(x^{(0)})$ versus iteration for a 1 subset version of the algorithm with precomputed curvatures as described in (68). The 4 subset version "converges" nearly 4 times faster than the 1 subset version. This acceleration factor is typical for ordered-subset methods.

Conclusion

A statistical method for reconstructing dual-energy X-ray CT images is described herein. The method is applicable to related tomographic imaging problems having energy diversity. The method can accommodate a very wide variety of statistical models and is likely to be sufficiently general to cover all useful choices since the mathematical assumptions on X are quite flexible.

Undoubtedly, many simplifications are possible for special cases of the above general framework. For simplicity, we have used an approximate physical model that ignores the nonlinearity caused by the exponential edge-gradient effect. Using optimization transfer methods similar to those used here, one could extend the algorithm derivation to account for this effect. Other blurring effects like detector after-glow, finite X-ray focal spot size, flying focal spot, detector response, could also be included.

Another extension would be to incorporate Compton scatter into the measurement model since a basis material formulation should facilitate model-based scatter approaches such as those used successfully in PET. The importance of scatter is well known.

Using a dual-energy approach eliminates the need for beam-hardening corrections, and the use of statistical methods also reduces metal artifacts.

As derived here, our final surrogate function is completely separable, both spatially and spectrally (in terms of the component density coefficients $x_{lj}$). It may be preferable to modify the derivation to only invoke spatial separation, but leave the spectral components coupled since they are jointly constrained so should be considered together.

The method is potentially applicable to all known dual-energy CT problems, including attenuation correction for PET-CT systems.

The invention relates to a method for statistical tomographic reconstruction from dual-energy X-ray CT scans or other sets of two or more transmission scans with differing energy spectra. This method has potential application in a variety of X-ray (and polyenergetic gamma ray) imaging applications, including medical X-ray CT, non-destructive evaluation in manufacturing, security purposes like baggage inspection, and accurate attenuation correction for PET scans from X-ray CT images.

Existing dual-energy methods are largely non-statistical and lead to unacceptably noisy images that have impeded their commercial adoption. Our statistical approach controls the noise by using more sophisticated modern iterative algorithms. This method extends the previously developed algorithm described in U.S. Pat No. 6,507,633 for reconstruction from single X-ray CT scans to the case of dual-energy scans.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for statistically reconstructing images from a plurality of transmission measurements having energy diversity, the method comprising:
   providing a plurality of transmission measurements having energy diversity; and
   processing the measurements with an algorithm based on a statistical model which accounts for the energy diversity to obtain at least one final component image which has reduced noise.

2. The method as claimed in claim 1, further comprising providing a cost function based on the statistical model wherein the cost function is minimized during the step of processing.

3. The method as claimed in claim 2, wherein the cost function has a gradient which is calculated during the step of processing.

4. The method as claimed in claim 3, wherein the gradient is calculated by backprojecting.

5. The method as claimed in claim 1, further comprising analyzing the at least one final component image.

6. The method as claimed in claim 1, further comprising calibrating spectra of the measurements to obtain calibration data wherein the step of processing utilizes the calibration data.

7. The method as claimed in claim 1, further comprising displaying the at least one final component image.

8. The method as claimed in claim 3, wherein the gradient is calculated by approximately using a subset of the measurements, such as an ordered subset of projection views, to accelerate the algorithm.

9. The method as claimed in claim 2, wherein the cost function has a regularizing penalty term.

10. The method as claimed in claim 1, wherein the measurements are dual-energy X-ray CT scans.

11. The method as claimed in claim 1, wherein the measurements are transmission scans with differing energy spectra, such as X-ray sources with different tube voltages or different filtrations, or gamma-ray sources with multiple energies.

12. The method as claimed in claim 2, wherein the cost function includes a log-likelihood term.

13. The method as claimed in claim 2, wherein the cost function consists solely of a log-likelihood function, which is called maximum likelihood reconstruction, or wherein the cost function consists of both a log-likelihood function and a regularizing penalty function, which is called penalized-likelihood or maximum a posteriori image reconstruction.

14. The method as claimed in claim 1, further comprising preprocessing the measurements prior to the step of processing to obtain preprocessed measurements and wherein the preprocessed measurements are processed in the step of processing to obtain the at least one component image.

15. The method as claimed in claim 12, wherein the log likelihood term is a function that depends on a model for an ensemble mean of the transmission measurements, and the model incorporates characteristics of an energy spectrum.

16. The method as claimed in claim 12, wherein the log-likelihood term is a function of the transmission measurements, prior to any pre-processing such as taking a logarithm of the measurements.

17. The method as claimed in claim 3, wherein the gradient of the cost function is calculated using a parametric approximation, such as polynomials, tables, or piecewise polynomials.

18. The method as claimed in claim 9, wherein the regularizing penalty term is based on quadratic functions of linear combinations of voxel values or nonquadratic (edge-preserving) functions of such combinations.

19. The method as claimed in claim 2, wherein parameter constraints such as non-negativity of voxel values are enforced during or after minimization of the cost function.

20. The method as claimed in claim 14, wherein the processing step is based on the preprocessed measurements and uses a cost function based on a statistical model for variability of the preprocessed measurements.

21. An image reconstructor apparatus for statistically reconstructing images from a plurality of transmission measurements having energy diversity, the apparatus comprising;
means for providing a plurality of transmission measurements having energy diversity; and
means for processing the measurements with an algorithm based on a statistical model which accounts for the energy diversity to obtain at least one final component image which has reduced noise.

22. The apparatus as claimed in claim 21, further comprising means for providing a cost function based on the statistical model wherein the cost function is minimized by the means for processing.

23. The apparatus as claimed in claim 22, further comprising means for calculating a gradient of the cost function.

24. The apparatus as claimed in claim 23, wherein the means for calculating calculates the gradient by backprojecting.

25. The apparatus as claimed in claim 21, further comprising means for analyzing the at least one final component image.

26. The apparatus as claimed in claim 21, further comprising means for calibrating spectra of the measurements to obtain calibration data wherein the means for processing utilizes the calibration data.

27. The apparatus as claimed in claim 21, further comprising a display for displaying the at least one final component image.

28. The apparatus as claimed in claim 23, wherein the means for calculating calculates the gradient approximately using a subset of the measurements, such as an ordered subset of projection views, to accelerate the algorithm.

29. The apparatus as claimed in claim 22, wherein the cost function has a regularizing penalty term.

30. The apparatus as claimed in claim 21, wherein the measurements are transmission scans with differing energy spectra, such as X-ray sources with different tube voltages or different filtrations, or gamma-ray sources with multiple energies.

31. The apparatus as claimed in claim 21, wherein the cost function includes a log-likelihood term.

32. The apparatus as claimed in claim 22, wherein the cost function consists solely of a log-likelihood function, which is called maximum likelihood reconstruction, or wherein the cost function consists of both a log-likelihood function and a regularizing penalty function, which is called penalized-likelihood or maximum a posteriori image reconstruction.

33. The apparatus as claimed in claim 22, wherein the cost function includes a maximum likelihood or penalized likelihood algorithm.

34. The apparatus as claimed in claim 21, further comprising means for preprocessing the measurements to obtain preprocessed measurements wherein the preprocessed measurements are processed by the means for processing to obtain the at least one component image.

35. The apparatus as claimed in claim 31, wherein the log likelihood term is a function that depends on a model for an ensemble mean of the transmission measurements, and the model incorporates characteristics of an energy spectrum.

36. The apparatus as claimed in claim 31, wherein the log-likelihood term is a function of the transmission measurements, prior to any preprocessing such as taking a logarithm of the measurements.

37. The apparatus as claimed in claim 23, wherein the gradient of the cost function is calculated using a parametric approximation, such as polynomials, tables, or piecewise polynomials.

38. The apparatus as claimed in claim 29, wherein the regularizing penalty term is based on quadratic functions of linear combinations of voxel values or nonquadratic (edge-preserving) functions of such combinations.

39. The apparatus as claimed in claim 22, wherein parameter constraints such as non-negativity of voxel values are enforced during or after minimization of the cost function.

40. The apparatus as claimed in claim 34, wherein the means for processing processes the preprocessed measurements and uses a cost function based on a statistical model for variability of the preprocessed measurements.

* * * * *